(12) United States Patent
Zhou et al.

(10) Patent No.: US 11,266,690 B2
(45) Date of Patent: Mar. 8, 2022

(54) CHIMERIC ANTIGEN RECEPTOR (CAR) BINDING TO BCMA, AND USES THEREOF

(71) Applicants: NANJING IASO BIOTHERAPEUTICS CO., LTD., Jiangsu (CN); INNOVENT BIOLOGICS (SUZHOU) CO., LTD., Jiangsu (CN)

(72) Inventors: Jianfeng Zhou, Jiangsu (CN); Junjian Liu, Jiangsu (CN); Guang Hu, Jiangsu (CN); Yongkun Yang, Jiangsu (CN); Guangrong Meng, Jiangsu (CN); Wenjing Gao, Jiangsu (CN); Yuyu Wang, Jiangsu (CN); Panpan Niu, Jiangsu (CN)

(73) Assignees: Nanjing IASO Biotherapeutics Co., Ltd., Jiangsu (CN); Innovent Biologics (Suzhou) Co., Ltd., Jiangsu (CN)

( * ) Notice: Subject to any disclaimer, the term of this patent is extended or adjusted under 35 U.S.C. 154(b) by 0 days.

(21) Appl. No.: 16/650,580

(22) PCT Filed: Jan. 31, 2019

(86) PCT No.: PCT/CN2019/074213
§ 371 (c)(1),
(2) Date: Mar. 25, 2020

(87) PCT Pub. No.: WO2019/149250
PCT Pub. Date: Aug. 8, 2019

(65) Prior Publication Data
US 2020/0246381 A1    Aug. 6, 2020

(30) Foreign Application Priority Data

Feb. 1, 2018   (CN) .......................... 201810100549.6
Oct. 19, 2018  (CN) .......................... 201811223693.5

(51) Int. Cl.
| | |
|---|---|
| *C07H 21/04* | (2006.01) |
| *C12N 15/63* | (2006.01) |
| *A61K 48/00* | (2006.01) |
| *A61K 35/17* | (2015.01) |
| *A61P 35/00* | (2006.01) |
| *C07K 14/725* | (2006.01) |
| *C07K 16/28* | (2006.01) |
| *C12N 15/62* | (2006.01) |
| *C12N 15/86* | (2006.01) |
| *A01K 67/00* | (2006.01) |

(52) U.S. Cl.
CPC .............. *A61K 35/17* (2013.01); *A61P 35/00* (2018.01); *C07K 14/7051* (2013.01); *C07K 16/2878* (2013.01); *C12N 15/62* (2013.01); *C12N 15/86* (2013.01)

(58) Field of Classification Search
CPC ..... A61K 35/17; A61P 35/00; C07K 16/2878; C12N 15/62; C12N 15/86
See application file for complete search history.

(56) References Cited

FOREIGN PATENT DOCUMENTS

| CN | 104379179 A | | 2/2015 |
|---|---|---|---|
| CN | 105777911 A | | 7/2016 |
| CN | 105837693 A | | 8/2016 |
| CN | 106687483 A | | 5/2017 |
| CN | 107207598 A | | 9/2017 |
| JP | 2017538710 A | | 12/2017 |
| WO | WO2005/000901 | * | 1/2005 |
| WO | WO2011/014469 | * | 2/2011 |
| WO | WO2013/138241 | * | 9/2013 |
| WO | WO2013/154760 | * | 10/2013 |
| WO | 2017181119 A2 | | 10/2014 |
| WO | WO2015/166105 | * | 11/2015 |
| WO | 2016094304 A2 | | 6/2016 |
| WO | 20160187349 A1 | | 11/2016 |
| WO | WO2017/029299 | * | 2/2017 |
| WO | WO2017/066122 | * | 4/2017 |
| WO | 20170149515 A1 | | 9/2017 |
| WO | 20170211900 A1 | | 12/2017 |
| WO | WO2020/223573 | * | 11/2020 |

OTHER PUBLICATIONS

Rudikoff et al. Single amino acid substitution altring antigen-binding specificity. PNAS USA 79:1979-1983, (Year: 1982).*
MacCallum et al. Antibody-antigen Interactions: Contact analysis and binding site topography. J. Mol. Biol. 262:732-745, (Year: 1996).*
Casset et al. A peptide mimetic of an anti-CD4 monoclonal antibody by rational design. Biochem. Biophys. Res. Commun. 307:198-205, (Year: 2003).*
Zhao et al. The application of CAR-T cell therapy in hematological malignancies: advantages and challenges. Acta Pharmaceutica Sinica B 8:539-551, (Year: 2018).*
Cho et al. BCMA CAR T-cell therapy arrives for multiple myeloma: a reality. Annals of Translational Medicine 6 (Suppl. 2): S93; doi: 10.21037/atm.2018.11.14, 5 pages, (Year: 2018).*
International Search Report dated May 5, 2019, Considered.

* cited by examiner

*Primary Examiner* — Quang Nguyen
(74) *Attorney, Agent, or Firm* — Honigman LLP; Thomas A. Wootton, Esq.; Jonathan P. O'Brien

(57) ABSTRACT

The invention provides a chimeric antigen receptor (CAR) which can specifically bind to a BCMA protein comprising a BCMA binding structural domain, a transmembrane domain, a costimulatory domain, and an intracellular signaling domain. The invention also provides uses of the CAR in treating diseases or conditions linked to the expression of BCMA.

30 Claims, 8 Drawing Sheets
Specification includes a Sequence Listing.

US 11,266,690 B2

CHIMERIC ANTIGEN RECEPTOR (CAR) BINDING TO BCMA, AND USES THEREOF

TECHNICAL FIELD

The present application relates to the field of biomedicine, and in particular to a chimeric antigen receptor capable of specifically binding to the BCMA protein.

BACKGROUND

The B-cell maturation antigen (BCMA), also known as CD269 or TNFRSF17, is a member of the tumor necrosis factor receptor family.

Studies have shown that BCMA can bind with a B-cell activating factor receptor (BAFF) and a B-cell proliferation-inducing ligand (APRIL) to promote the survival of B cells at different stages of development. Abnormal signal transduction may result in the abnormal proliferation of B cells, leading to autoimmune diseases and tumorigenesis (see Rickert, et al., Immunological Reviews, 2011, Vol. 244: 115-133).

The chimeric antigen receptor (CAR) is an antigen receptor that is designed to identify a cell surface antigen in a human leucocyte antigen-independent manner. Some progress has been made in the attempts to treating such patients with CAR-expressing T cells (CAR-T) (Molecular Therapy, 2010, 18:4, 666-668; Blood, 2008, 112: 2261-2271).

Given the effectiveness of the BCMA being used as a therapeutic target in B-cell malignancies, and particularly in multiple myelomas, there is an urgent need in the art to develop a new cellular therapy to achieve the treatment goal by acting on the BCMA.

SUMMARY

The present application provides a chimeric antigen receptor capable of specifically binding to the BCMA and an application thereof. The BCMA chimeric antigen receptor provided by the present application has one or more of the following properties: 1) a higher affinity to the BCMA protein; 2) the CAR being able to be stably expressed in CAR-T cells that are prepared with the CAR; 3) a higher GFP positive rate in the CAR-T cells that are prepared with the CAR; 4) the release of cytokines being promoted by the CAR; 5) the chimeric antigen receptor being able to be used to treat diseases or conditions associated with the expression of BCMA.

In one aspect, the present application includes a chimeric antigen receptor (CAR), wherein the CAR contains a BCMA-binding domain, a transmembrane domain, a costimulatory domain and an intracellular signal transduction domain, the BCMA-binding domain comprises an antibody or a fragment thereof capable of specifically binding a BCMA, and the antibody contains a heavy chain complementary determining region 1 (HCDR1), a heavy chain complementary determining region 2 (HCDR2) and a heavy chain complementary determining region 3 (HCDR3), wherein the HCDR1 comprises an amino acid sequence of SEQ ID NO: 9, the HCDR2 comprises an amino acid sequence of SEQ ID NO: 10, and the HCDR3 comprises an amino acid sequence of SEQ ID NO: 11.

In some embodiments, the antibody contains a light chain complementary determining region 1 (LCDR1), a light chain complementary determining region 2 (LCDR2) and a light chain complementary determining region 3 (LCDR3), and wherein the LCDR1 comprises an amino acid sequence of SEQ ID NO: 17, the LCDR2 comprises an amino acid sequence of SEQ ID NO: 18, and the LCDR3 comprises an amino acid sequence of SEQ ID NO: 19. In some embodiments, the antibody contains a heavy chain variable region, and the heavy chain variable region comprises an amino acid sequence of SEQ ID NO: 7. In some embodiments, the antibody contains a light chain variable region, and the light chain variable region comprises an amino acid sequence of SEQ ID NO: 15. In some embodiments, the antibody is a single-chain antibody fragment. In some embodiments, the antibody comprises an amino acid sequence of SEQ ID NO: 43.

In some embodiments, the transmembrane domain of the CAR includes transmembrane domains derived from proteins selected from a group of consisting of α, β or ζ chain of the T cell receptor, CD28, CD3e, CD45, CD4, CD5, CD8a, CD9, CD16, CD22, CD33, CD37, CD64, CD80, CD86, CD134, CD137 and CD154. In some embodiments, the transmembrane domain comprises an amino acid sequence of SEQ ID NO: 27.

In some embodiments, the costimulatory domain of the CAR includes costimulatory domains derived from proteins selected from a group consisting of CD28, 4-1BB, OX-40 and ICOS. In some embodiments, the costimulatory domain contains an amino acid sequence of SEQ ID NO: 29 or SEQ ID NO: 31.

In some embodiments, the intracellular signal transduction domain of the CAR includes a signal transduction domain derived from CD3ζ. In some embodiments, the intracellular signal transduction domain contains an amino acid sequence of SEQ ID NO: 33.

In some embodiments, the CAR also contains a hinge region that links the BCMA-binding domain to the transmembrane domain. In some embodiments, the hinge region contains an amino acid sequence of SEQ ID NO: 25.

In some embodiments, the CAR is also linked to a signal peptide. In some embodiments, the signal peptide contains an amino acid sequence of SEQ ID NO: 3.

In some embodiments, the CAR is also linked to a cleaving peptide. In some embodiments, the cleaving peptide contains an amino acid sequence derived from a T2A peptide. In some embodiments, the cleaving peptide contains an amino acid sequence of SEQ ID NO: 35.

In some embodiments, the CAR contains an amino acid sequence of SEQ ID NO: 49 or SEQ ID NO: 51.

In another aspect, the present application further comprises an isolated nucleic acid molecule encoding the CAR described in the present application.

In another aspect, the present application also includes an isolated nucleic acid molecule encoding the CAR, which contains a nucleotide sequence of SEQ ID NO: 50 or SEQ ID NO: 52.

In another aspect, the present application also includes a vector, which contains the nucleic acid molecule of the present application. In some embodiments, the vector is selected from a plasmid, a retroviral vector and a lentiviral vector.

In another aspect, the present application also comprises an immune effector cell, which contains the CAR of the present application, the nucleic acid molecule of the present application, or the vector of the present application. In some embodiments, the immune effector cell is selected from a T lymphocyte and a natural killer (NK) cell.

In another aspect, the present application also comprises a method of preparing an immune effector cell, which includes introducing the vector of the present application into the immune effector cell.

In another aspect, the present application further includes a composition, which contains the immune effector cell of the present application.

In another aspect, the present application further comprises a use of the CAR, the nucleic acid molecule, the vector or the immune effector cell in the preparation of drugs used to treat diseases or conditions associated with the expression of BCMA. In some embodiments, the diseases or conditions associated with the expression of BCMA are cancers or malignant tumors.

Other aspects and advantages of the present application will be readily apparent to those skilled in the art from the following detailed description. Only the exemplary embodiments of the present application are shown and described in the following detailed description. The content of the present application enables those skilled in the art to modify the disclosed specific embodiments without departing from the spirit and scope of the invention involved in the present application, as will be realized by those skilled in the art. Accordingly, the drawings of the present application and description in the specification are merely intended to be illustrative and not restrictive.

DETAILED DESCRIPTION

Figure 1:
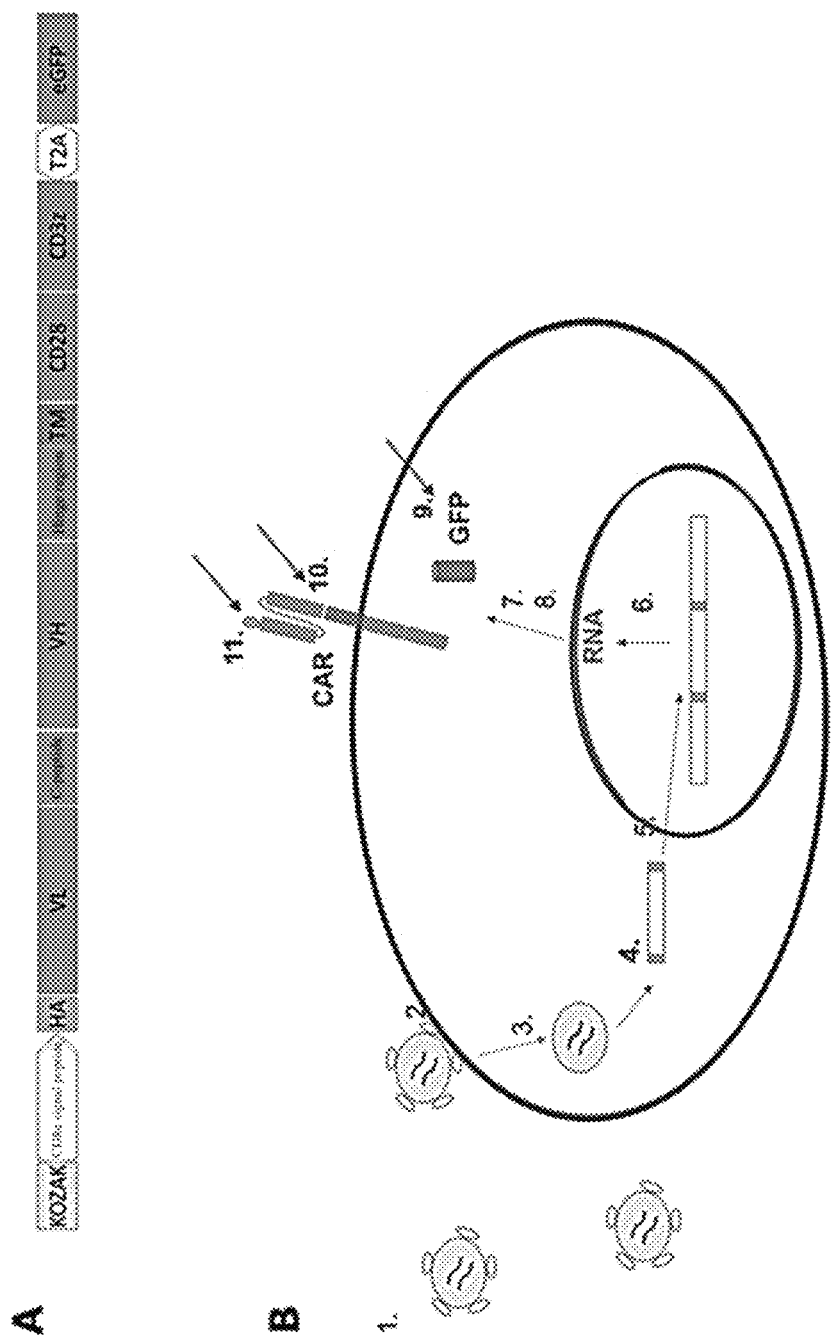
FIG. 1A shows a structure of the CAR of the present application.
FIG. 1B shows the evaluation result of the expression of the CAR of the present application through a GFP signal.

The embodiments of the invention of the present application will be described hereinafter through specific examples. Those skilled in the art can easily appreciate other advantages and effects of the invention of the present application from the disclosure of the specification. The CAR of the present application can specifically bind to the BCMA, CAR-T cells that are prepared with the CAR can stably express the CAR, and the CAR-T cells that are prepared with the CAR have a higher CAR positive rate. In addition, the CAR can promote the release of cytokines, and is able to be used to treat diseases or conditions associated with the expression of BCMA.

The methods of conventional chemistry, biochemistry, organic chemistry, molecular biology, microbiology, recombinant DNA technique, genetics, immunology and cytobiology within the skill of the art are adopted to implement the present application unless otherwise explicitly indicated. The description of these methods can be found, for example, in Sambrook, et al., Molecular Cloning: A Laboratory Manual (3rd edition, 2001); Sambrook, et al., Molecular Cloning: A Laboratory Manual (2nd edition, 1989); Maniatis, et al., Molecular Cloning: A Laboratory Manual (1982); Ausubel, et al., Current Protocols in Molecular Biology (John Wiley and Sons, updated in July, 2008); Short Protocols in Molecular Biology: A Compendium of Methods from Current Protocols in Molecular Biology, Greene Pub. Associates and Wiley-Interscience; Glover, DNA Cloning: A Practical Approach, vol.I&II (IRL Press, Oxford, 1985); Anand, Techniques for the Analysis of Complex Genomes, (Academic Press, New York, 1992); Transcription and Translation (B. Hames&S. Higgins, Eds., 1984); Perbal, A Practical Guide to Molecular Cloning (1984); Harlow and Lane, Antibodies, (Cold Spring Harbor Laboratory Press, Cold Spring Harbor, N.Y., 1998) Current Protocols in Immunology Q. E. Coligan, A. M. Kruisbeek, D. H. Margulies, E. M. Shevach and W. Strober, eds., 1991); Annual Review of Immunology; and periodicals and monographs such as Advances in Immunology.

Unless otherwise defined, the meanings of all the technological and scientific terms used in the present application are the same as those generally understood by those of ordinary skill in the art. For the purpose of the present application, the following terms are defined.

In the present application, the term "chimeric antigen receptor (CAR)" generally refers to a fusion protein that contains an extracellular domain capabal of binding with an antigen and at least one intracellular domain. The CAR is a core part of a chimeric antigen receptor T cell (CAR-T), and may contain an antigen (such as a tumor-associated antigen (TAA)) binding domain, a transmembrane domain, a costimulatory domain and an intracellular signal domain. In the present application, the CAR may be combined with a T cell receptor-activating intracellular domain specifically based on the antigen (such as a BCMA) of an antibody. The genetically-modified CAR-expressing T cells can specifically identify and eliminate target antigen-expressing malignant cells. The description of the CAR and the CAR-T cells can be found, for example, in Sadelain M, Brentjens R, Rivi'ere I. The basic principles of chimeric antigen receptor design. Cancer Discov. 2013; 3(4): 388-398; Turtle C J, Hudecek M, Jensen M C, Riddell S R. Engineered T cells for anti-cancer therapy. Curr Opin Immunol. 2012; 24(5): 633-639; Dotti G, Gottschalk S, Savoldo B, Brenner M K. Design and development of therapies using chimeric antigen receptor-expressing T cells. Immunol Rev. 2014; 257(1): 107-126; WO2013154760 and WO2016014789.

In the present application, the terms "BCMA" and "B-cell maturation antigen" may be used interchangeably, and generally refer to a protein encoded by TNFRSF17 gene. The BCMA protein is a member of the tumor necrosis factor receptor family. In the present application, the BCMA may be a human BCMA, with a GenBank accession number of BAB60895.1. The BCMA is a type-III transmembrane protein, and possesses a cysteine-rich domain (CRD) characterizing members of the TNFR family in extracellular domain (ECD), which forms a ligand-binding motif. As a B-cell biomarker, the BCMA is expressed in a tumor cell (such as a multiple myeloma cell) or located on the surface of a tumor cell (for example, a malignant plasmocyte of multiple myeloma). The BCMA protein may also comprise a fragment of the BCMA, such as an extracellular domain and a fragment thereof, such as a binding domain, a transmembrane domain, a costimulatory domain, and an intracellular signal transduction domain and a fragment able to bind with any antibody of the present application.

In the present application, the term "BCMA-binding domain" generally refers to a domain that can specifically bind to the BCMA protein. For example, the extracellular BCMA-binding domain may comprise a chimeric antigen receptor or a fragment thereof capable of specifically binding to a human BCMA polypeptide expressed on a B cell or, as well as an anti-BCMA antibody or an antigen-binding fragment thereof. Terms "binding domain", "extracellular domain", "extracellular binding domain", "antigen-specific binding domain" and "extracellular antigen-specific binding domain" used in the present application can be used interchangeably, and provide a CAR domains or fragments having the ability to specifically bind to a target antigen (such as BCMA). The BCMA-binding domain may be derived from a natural source, a synthetic source, a semi-synthetic source or a recombinant source.

In the present application, the term "antibody" generally refers to a polypeptide molecule capable of specifically identifying and/or neutralizing a specific antigen. For example, the antibody may comprise an immunoglobulin consisting of at least two heavy (H) chains and two light (L) chains that are connected to each other via disulfide bonds, and comprise any molecule containing an antigen-binding part thereof. The term "antibody" comprises monoclonal antibodies, antibody fragments or antibody derivatives, including but not limited to human antibodies, humanized antibodies, chimeric antibodies, single-domain antibodies (such as dAb), single-chain antibodies (such as scFv) and antigen-binding antibody fragments (such as Fab, Fab' and (Fab)2 fragments). The term "antibody" further comprises all recombinant forms of the antibody, such as an antibody expressed in prokaryotic cells, an unglycosylated antibody, as well as any antigen-binding antibody fragment of the present application and derivatives thereof. Each heavy chain can be composed of a heavy chain variable region (VH) and a heavy chain constant region. Each light chain can be composed of a light chain variable region (VL) and a light chain constant region. The VH and VL can be further divided into hypervariable regions known as complementary determining regions (CDR), which are scattered in more-conserved regions known as framework regions (FR). Each of the VH and VL can be composed of three CDRs and four FRs, which may be arranged from the amino terminal to the carboxyl terminal according to the following order: FR1, CDR1, FR2, CDR2, FR3, CDR3 and FR4. The variable regions of heavy chains and light chains comprise a binding domain interacting with antigens. The constant regions of the antibody may mediate the binding of the immunoglobulin to a host tissue or factor that comprises a variety of cells (such as effector cells) of the immune system and a first component (Clq) of the classical complement system.

In the present application, the term "antigen-binding molecule" generally refers to a molecule containing an antigen-binding region or antigen-binding part capable of binding a target antigen, such as a protein or a polypeptide. In the present application, when the target antigen is a B-cell maturation antigen (BCMA), the antigen-binding molecule binding BCMA is also called as a BCMA-binding molecule. The antigen-binding molecules include, for example, antibodies and antigen-binding fragments thereof, single-chain scFv antibodies, as well as various fusions and conjugates constructed based on scFv (such as scFv-Fc antibodies, immunoconjugates, antibody-drug conjugates (ADCs), multispecific/bispecific antibodies, and chimeric antigen receptors (CARs)). As known by those skilled in the art, the antigen-binding part of the antibody generally comprises an amino acid residue derived from the "complementary determining regions" or "CDRs". In some cases, "BCMA-binding molecule" and "antibody of the present application" or "anti-BCMA antibody" may be used interchangeably according to the context.

In the present application, the term "single-chain antibody fragment" may be an antibody that is formed by the heavy chain variable regions and the light chain variable regions connected via a C-peptides.

In the present application, the term "transmembrane domain" generally refers to a domain in the CAR that passes through the cell membrane and is linked to the intracellular signal transduction domain, playing a role of signaling.

In the present application, the term "costimulatory domain" generally refers to an intracellular domain capable of providing an immunocostimulatory molecule, and the immunocostimulatory molecule is a cell surface molecule required in the effective response of lymphocytes to an antigen. The costimulatory domain mentioned may include a costimulatory domain of CD28, and may also include costimulatory domains of the TNF receptor family, such as costimulatory domains of CD28, OX40, 4-1BB or ICOS.

In the present application, the term "hinge region" generally refers to a connecting region between an antigen-binding region and an immunocyte Fc receptor (FcR)-binding region.

In the present application, the term "HA-tag" generally refers to a protein tag based on a human influenza hemagglutinin antigen, and its chemical nature is a short amino acid sequence derived from human influenza hemagglutinin amino acids 98-106. After a method of molecular biology is adopted to splice the HA-tag sequence to one terminal of a target protein, an anti-HA-tag specific antibody can be used to bind with the recombinant protein, which is favorable for the conduct of experiments such as immunohistochemistry (IHC), Western Blotting, etc. (see Schembri, Laura, et al., The HA tag is cleaved and loses immunoreactivity during apoptosis. Nature Methods. February 2007, 4 (2): 107-108).

In the present application, the term "intracellular signal transduction domain" generally refers to a domain that is located inside a cell and can transduce signals. In the present application, the intracellular signal transduction domain can transduce signals into the cell. For example, the intracellular signal transduction domain is an intracellular signal transduction domain of the chimeric antigen receptor. For example, in some embodiments, the intracellular signal transduction domain may be selected from a group consisting of a CD3 intracellular domain, a CD28 intracellular domain, a 4-1BB intracellular domain and an OX40 intracellular domain.

In the present application, the term "signal peptide" generally refers to a peptide chain for guiding the protein transfer. In some embodiments, the signal peptide may be a short peptide chain, which have a length of 5 to 30 amino acids.

In the present application, the term "cleaving peptide" refers to a type of polypeptides that is able to implement a protein cleaving function. For example, the cleaving peptide can achieve the protein cleaving by ribosome skipping rather than protease hydrolysis. For example, the cleaving peptide mentioned may be cleaving 2A peptides that may include T2A, F2A, P2A, etc.

In the present application, the term "marker detection signal" generally refers to a gene, a protein or other molecules with known functions and sequences that can play the role of a specific marker and emit detectable signals. The marker detection signal may be fluorescent proteins, such as GFP, RFP, YFP, etc. The marker detection signal mentioned may be EGFRt.

In the present application, the term "EGFRt" generally refers to a gene encoding a truncated human epidermal growth factor receptor polypeptide. The EGFRt lacks a membrane-distal EGF-binding domain and a cytoplasmic signal transduction tail, but keeps an extracellular epitope identified by an anti-EGFR antibody. The EGFRt can be used as a non-immunogenic selection tool with a function of genetically modifying cells and a tracking marker. In the present application, the EGFRt may serve as a marker molecule for a CAR-T cell. The EGFRt mentioned may eliminate the cetuximab-mediated ADCC pathway for the CAR-T cells in the body if necessary (see U.S. Pat. No. 8,802,374B2).

In the present application, the term "Kozak sequence" generally refers to a (gcc)gccRccAUGG sequence that is common in the mRNAs of eukaryotes. The Kozak sequence plays an important role in initiating the translation process, and is identified as a translation initiation site by ribosomes (see, De Angioletti M, et al., a novel silent beta-thalassaemia mutation, the first in the Kozak sequence. Br J Haematol. 2004, 124 (2): 224-31.).

In the present application, the term "isolated" generally means that an antibody which has been separated from its components in the natural environment. In some embodiments, the antibody is purified to have a purity of higher than 95% or 99%, which is determined by, for example, electrophoresis (such as SDS-PAGE, isoelectric focusing (IEF) or capillary electrophoresis) or chromatography (such as ion exchange or reversed-phase HPLC). The overview of the method for evaluating the antibody purity can be found in Flatman, S. et al, J. Chrom. B 848 (2007) 79-87.

In the present application, the term "nucleic acid molecule" generally refers to an isolated nucleotide, deoxyribonucleotide or ribonucleotide of any length that is isolated from a natural environment thereof or is artificially synthesized, or an analogue thereof. The nucleic acid molecule of the present application may be isolated. For example, the nucleic acid molecule can be produced or synthesized by the following methods: (i) in-vitro amplification, such as polymerase chain reaction (PCR) amplification; (ii) cloning and recombination; (iii) purification, such as digestion and gel electrophoresis separation; or (4) synthesis, such as chemical synthesis. In some embodiments, the isolated nucleic acid is a nucleic molecule prepared by the recombinant DNA technology. In the present application, the nucleic acid encoding the antibody or the antigen-binding fragment thereof can be prepared by a variety of methods known in the art, including but not limited to adopting restriction fragment operation or overlap extension PCR of synthesized oligonucleotide. The specific operation can be found in Sambrook, et al., Molecular Cloning, A Laboratory Manual, Cold Spring Harbor Laboratory Press, Cold Spring Harbor, N.Y., 1989; and Ausube, et al., Current Protocols in Molecular Biology, Greene Publishing and Wiley-Interscience, New York N.Y., 1993.

In the present application, the "vector" generally refers to a nucleic acid molecule capable of self-replicating in a suitable host, and it is used to transfer the inserted nucleic acid molecules into host cells and/or the intercellular substance between host cells. The vector may comprise a vector mainly used for inserting DNA or RNA into cells, a vector mainly used for replicating DNA or RNA, and a vector mainly used for the expression of transcription and/or translation of DNA or RNA. The vector further includes a vector with a variety of the aforementioned functions. The vector may be a polynucleotide which can be transcribed and translated into a polypeptide when it is introduced into a suitable host cell. Generally, the vector can produce a desirable expression product by culturing the suitable host cell containing the vector. In the present application, the vector may contain one or more types of the nucleic acid molecules. In addition, the vector may further contain other genes, for example, a marker gene allowing the vector to be selected in a suitable host cell and an appropriate condition. In addition, the vector may also contain an expression control element that allows the coding region to be correctly expressed in a suitable host. Such a control element is well-known to those skilled in the art, and, for example, can include a promoter, a ribosome-binding site, an enhancer, and other control elements for regulating gene transcription or mRNA translation. In some embodiments, the expression control sequence is a regulable element. The specific structure of the expression control sequence can be varied according to the functions of species or cell types, but generally contains a 5' non-transcribed sequence and 5' and 3' non-translated sequences which participate in the transcription initiation and the translation initiation respectively, such as a TATA box, a capped sequence, a CAAT sequence, etc. For example, 5' non-transcribed expression control sequence can contain a promoter region, which can comprise a promoter sequence for transcribing and controlling functionally-linked nucleic acids. The vector of the present application can be selected from a plasmid, a retroviral vector and a lentiviral vector. The plasmid, retroviral vector and lentiviral vector of the present application can contain the CAR.

In the present application, the term "plasmid" generally refers to a DNA molecule other than chromosomes or nucleoids in organisms such as bacteria, saccharomycetes, etc. Plasmids, which can exist in cytoplasm, have the capability of self-replicating, so that a constant copy number therefor can be kept in offspring cells and the carried genetic information can be expressed. Plasmids can be used as vectors for genes in genetic engineering researches.

In the present application, the term "retroviral vector" generally refers to a virion that can control and express exogenous genes but cannot be self-packaged to have the proliferation capability. Most of such viruses have reverse transcriptase. A retrovirus comprises at least three types of genes: gag, comprising a gene for proteins forming the viral core and structure; pol, comprising a gene for reverse transcriptase and env, comprising a gene forming virus coat. The genome of the retroviral vector itself and an exogenous gene carried by it can be randomly and stably integrated into the genome of a host cell through the retrovirus transfection, for example, the CAR molecule may be integrated into the host cell.

In the present application, the term "lentiviral vector" generally refers to a diploid RNA viral vector that belongs to the retrovirus. The lentiviral vector is a vector that is prepared by removing multiple sequence structures associated with virus activity in the genome of a lentivirus to provide the genome with biological safety and then introducing the sequence and expression structure of a target gent needed by an experiment into this genome framework. The genome of the retroviral vector itself and an exogenous gene carried by it can be randomly and stably integrated into the genome of a host cell through the lentiviral vector transfection, for example, the CAR molecule can be integrated into the host cell.

In the present application, the term "transposon" generally refers to a discrete DNA fragment containing a transposase gene. The flanking sequences are terminal inverted repeats (TIRs) containing transposase-binding sites. The transposase can bind with a TIR and transfer the transposon to a new site. The transposon of the present application is a double-component system composed of a CAR-carrying plasmid (transposon) and a transposase-carrying plasmid. The transposon may be introduced into a target cell by electric transduction or other methods. For example, the two components are first electroporated into a peripheral blood mononuclear cell (PBMC), and the expressed transposase acts on the terminal inverted repeats (TIRs) on both sides of the CAR, so that the CAR (transposon) is cut and then integrated onto the TA dinucleotide sequence in the genome of the target cell (such as a T cell). After the transposition and the stable genome integration are complete, a CAR protein can be expressed on the surface of the target cell (see Cheng Zhang, Jun Liu, Jiang F Zhong, et al. Engineering CAR-T cells. Biomarker Research. 2017, 5: 22).

In the present application, the term "gene editing" generally refers to a technique for site-directed modification of a targeted genome. The gene editing may include techniques based on zinc finger nucleases (ZFNs), transcription activator like effector nucleases (TALENs), clustered regularly interspaced short palindromic repeats/CRISPR-associated (Cas9), CRISPR/Cas9), etc. The gene editing can achieve the highly efficient targeted modification on a genome by adding, removing or changing the genetic material at a specific position of a genome. The gene editing of the present application can comprise introducing the CAR molecule into the genome of a recipient cell by a gene editing technique (such as CRISPR-Cas9).

In the present application, the term "immune effector cell" generally refers to an immunocyte that participates in removing foreign antigens and performing an effector function in the immune response. For example, in some embodiments, the immune effector cell may be a plasmocyte, a cytotoxic T cell, a NK cell, an APSC pluripotent cell, a mast cell, etc. In the present application, the immune effector cell can be selected from a T lymphocyte and a natural killer (NK) cell.

In the present application, the term "pharmaceutically acceptable adjuvant" generally refers to a pharmaceutically acceptable preparation vector, solution or additive for enhancing preparation properties. Such additives are well-known to those skilled in the art.

In the present application, the term "cancer" generally refers to or describes the physiological condition of a mammal, and it is typically characterized in cell proliferation or survival disorder. In the present application, hyperproliferative diseases known as cancers include but are not limited to solid tumors, such as cancers occurring in breasts, respiratory tracts, brains, reproductive organs, alimentary canals, urethrae, eyes, livers, skins, heads and necks, thyroid glands and parathyroid glands, as well as distant metastases thereof. Such diseases also include lymphomas, sarcomas and leukemias. The examples of breast cancers include but are not limited to invasive ductal carcinoma, invasive lobular carcinoma, ductal carcinoma in situ and lobular carcinoma in situ. The examples of respiratory tract cancers include but are not limited to small cell lung cancer, non-small cell lung cancer, bronchial adenoma and pleuropulmonary blastoma. The examples of brain cancers include but are not limited to brain stem and hypothalamic gliomas, cerebellar and cerebral astrocytomas, medulloblastoma, ependymoma and neuroectodermal and pineal tumors. Male genital neoplasms include but are not limited to prostatic cancers and testicular cancers. Female genital neoplasms include but are not limited to endometrial cancer, cervical cancer, ovarian cancer, vaginal cancer, vulvar cancer and hysteroma. Gastrointestinal tumors include but are not limited to anal cancer, colon cancer, colorectal cancer, esophageal cancer, gallbladder cancer, stomach cancer, pancreatic cancer, rectal cancer, small intestine cancer and salivary gland cancer. Urethral tumors include but are not limited to bladder cancer, penile cancer, renal carcinoma, renal pelvic carcinoma, ureteral cancer and urethral cancer. Eye cancers include but are not limited to intraocular melanoma and retinoblastoma. The examples of liver cancers include but are not limited to hepatocellular carcinoma (hepatocellular carcinoma with or without fibrolamellar variation), cholangiocarcinoma (intrahepatic cholangiocarcinoma) and combined hepatocellular-cholangiocarcinoma. Skin cancers include but are not limited to squamous-cell carcinoma, Kaposi's sarcoma, malignant melanoma, Merkel cell carcinoma and non-melanoma skin cancers. Head and neck cancers include but are not limited to laryngeal/hypopharyngeal/nasopharyngeal/oropharyngeal carcinomas, as well as lip and oral cancers. Lymphomas include but are not limited to AIDS-associated lymphoma, non-Hodgkin's lymphoma, cutaneous T-cell lymphoma, Hodgkin's disease and central nervous system lymphoma. Sarcomas include but are not limited to soft tissue sarcoma, osteosarcoma, malignant fibrous histiocytoma, lymphosarcoma and rhabdomyosarcoma. Leukemias include but are not limited to acute myeloid leukemia, acute lymphocytic leukemia, chronic lymphocytic leukemia, chronic myelocytic leukemia and hairy cell leukemia.

The term "and/or" should be understood as any one of the options or both of the options.

As used in the present application, the term "comprise" or "include" is intended to encompass the described elements, integers or steps, but does not exclude any other elements, integers or steps. In the present application, when the term "comprise" or "include" is used, it encompasses a case composed of the elements, integers or steps unless otherwise specified. For example, when it relates to "comprising" the antibody variable region of a certain specific sequence, it is also intended to cover an antibody variable region composed of the specific sequence.

In the present application, the term "about" generally refers to a variation within a range of 0.5%-10% above or below a specified value, for example, a variation within a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% above or below a specified value.

Chimeric Antigen Receptor

In the present application, the chimeric antigen receptor (CAR) may comprise an extracellular domain of a BCMA, a transmembrane domain, a costimulatory domain and an intracellular signal transduction domain. In the present application, the extracellular domain of the CAR may comprise the single-chain antibody fragment (scFv) of the present application. For example, the single-chain antibody fragment may be linked to the transmembrane domain through a hinge region (such as a CD8 hinge). In the present application, the CAR may be used to transduce an immune effector cell (such as a T cell), and be expressed on the cell surface. Thus, the present application can also provide a T cell expressing the chimeric antigen receptor, as well as a use of the T cell and/or the CAR in the preparation of drugs for treating B cell-associated diseases.

In the present application, the chimeric antigen receptor (CAR) may comprise a BCMA-binding domain, a transmembrane domain, a costimulatory domain and an intracellular signal transduction domain.

In the present application, the BCMA-binding domain may comprise an antibody fragment capable of specifically binding a BCMA, and the antibody may comprise a heavy chain complementary determining region 1 (HCDR1), a heavy chain complementary determining region 2 (HCDR2) and a heavy chain complementary determining region 3 (HCDR3), wherein the HCDRs 1-3 may comprise amino acid sequences of SEQ ID NOs: 9-11 in sequence; the antibody may also comprise a light chain complementary determining region 1 (LCDR1), a light chain complementary determining region 2 (LCDR2) and a light chain complementary determining region 3 (LCDR3), and the LCDRs 1-3 may comprise amino acid sequences of SEQ ID NOs: 17-19 in sequence. In the present application, the antibody may comprise a heavy chain variable region that may comprise an amino acid sequence of SEQ ID NO: 7. In the present application, the antibody may comprise a light chain variable region that may comprise an amino acid sequence of SEQ ID NO: 15.

In the present application, the antibody may be a single-chain antibody fragment. In some embodiments, the antibody may comprise an amino acid sequence of SEQ ID NO: 43. For example, the antibody of the present application or the antigen-binding fragment may include an antibody scFv0032 with a sequence of SEQ ID NO: 43.

For example, the single-chain antibody fragment of the present application may be scFv0032 with a sequence of SEQ ID NO: 43. The LCDRs 1-3 of the single-chain antibody fragment scFv0032 comprise an amino acid sequence of SEQ ID NO: 17, SEQ ID NO: 18 and SEQ ID NO: 19 respectively; the VL comprises an amino acid sequence of SEQ ID NO: 15; the HCDRs 1-3 comprise an amino acid sequence of SEQ ID NO: 9, SEQ ID NO: 10 and SEQ ID NO: 11 respectively; and the VH comprise an amino acid sequence of SEQ ID NO: 7.

The CAR of the present application may comprise a transmembrane domain, and the transmembrane domain may comprise a transmembrane domain derived from proteins selected from a group consisting of α, β or ζ chain of the T cell receptor, CD28, CD3e, CD45, CD4, CD5, CD8a, CD9, CD16, CD22, CD33, CD37, CD64, CD80, CD86, CD134, CD137 and CD154. In the present application, the transmembrane domain may comprise an amino acid sequence of SEQ ID NO: 27 or functional variants thereof. For example, the transmembrane domain of the present application may comprise CD8a, with a sequence of SEQ ID NO: 27.

The CAR of the present application may comprise a costimulatory domain that may contain a polypeptide derived from a protein selected from a group consisting of CD28, 4-1BB, OX-40 and ICOS. In the present application, the costimulatory domain may comprise an amino acid sequence of SEQ ID NO: 29 or SEQ ID NO: 31.

The CAR of the present application can contain an intracellular signal transduction domain, and the intracellular signal transduction domain can include a signal transduction domain derived from CD3ζ. In the present application, the intracellular signal transduction domain may comprise an amino acid sequence of SEQ ID NO: 33.

The CAR of the present application may contain a hinge region that links the antibody and the transmembrane domain. In the present application, the hinge region may comprise an amino acid sequence of SEQ ID NO: 25.

The CAR of the present application may also comprise an HA-tag that may be located at the N terminal of the CAR. In the present application, the HA-tag may comprise an amino acid sequence of SEQ ID NO: 5. In the present application, an anti-HA antibody may be used to specifically bind with the CAR so as to assay the expression of the CAR of the present application and enrich the CAR-T cell for functionality study.

The CAR of the present application may be linked to a signal peptide that may comprise an amino acid sequence of SEQ ID NO: 3. For example, the signal peptide may be a CD8a signal peptide with a sequence of SEQ ID NO: 3. For example, CAR0043, CAR0097 and CAR0099 may be linked to the CD8a signal peptide.

In the present application, the CAR may also be linked to a cleaving peptide. In the present application, the cleaving peptide may comprise an amino acid sequence derived from a T2A peptide. In the present application, the cleaving peptide may comprise an amino acid sequence may comprise SEQ ID NO: 35. For example, the cleaving peptide may be a T2A with a sequence of SEQ ID NO: 35. For example, CAR0043 and CAR0099 can be linked to the cleaving peptide T2A.

In the present application, the CAR may also be linked to a marker detection signal that may be located at the C terminal of the CAR. In the present application, the marker detection signal may be a fluorescent protein, which may be selected from a group consisting of GFP, RFP and YFP. In the present application, the expression of CAR molecules may be indirectly evaluated by detecting the GFP signal. For example, the CAR may comprise CAR0043 with a marker detection signal sequence of SEQ ID NO: 37. In the present application, the marker detection signal may be EGFRt. For example, CAR0099 may be linked to a marker detection signal with a sequence of SEQ ID NO: 39.

In the present application, the CAR may be linked to a Kozak sequence with a sequence of SEQ ID NO: 1. In the present application, the CAR may be linked to a Kozak sequence that may be located at the N terminal of the CAR. For example, CAR0043, CAR0097 or CAR0099 can be linked to a Kozak sequence with a sequence of SEQ ID NO: 1.

In the present application, the CAR may comprise an amino acid sequence of SEQ ID NO: 49 or SEQ ID NO: 51. For example, the CAR may be selected from CAR0043 with a sequence of SEQ ID NO: 49. As another example, the CAR may be selected from CAR0097 with a sequence of SEQ ID NO: 51; and the CAR may be selected from CAR0099 with a sequence of SEQ ID NO: 51.

In certain embodiments, the CAR of the present application may comprise a BCMA-binding domain, a transmembrane domain, a costimulatory domain and an intracellular signal transduction domain in sequence. The CAR may comprise a BCMA-binding domain, and the BCMA-binding domain comprises a sequence of SEQ ID NO: 43. The BCMA-binding domain may comprise HCDRs 1-3 with sequences of SEQ ID NOs: 9-11 in sequence, and the BCMA-binding domain may comprise LCDRs 1-3 with sequences of SEQ ID NO: 17-19 in sequence; and the BCMA-binding domain may comprise a heavy chain variable region with a sequence of SEQ ID NO: 7; and the BCMA-binding domain may also comprise a light chain variable region with a sequence of SEQ ID NO: 15. For example, the CAR can include CAR0043, CAR0097, CAR0099 or a CAR of the present application having the same light chain variable region and heavy chain variable region as them. A C-peptide may also be comprised between the light chain variable region and the heavy chain variable region, which has a sequence shown as SEQ ID NO: 23. For example, the CAR may comprise CAR0043, CAR0097, CAR0099 or a CAR of the present application having the same C-peptide as them.

The transmembrane domain may comprise a transmembrane domain, and the transmembrane domain comprises a polypeptide derived from a protein selected from a group consisting of α, β or ζ chain of the T cell receptor, CD28, CD3e, CD45, CD4, CD5, CD8a, CD9, CD16, CD22, CD33, CD37, CD64, CD80, CD86, CD134, CD137 and CD154, and the transmembrane domain may comprises a sequence of SEQ ID NO: 27. For example, the transmembrane domain may be CD8a, and the CAR may comprise CAR0043, CAR0097, CAR0099 or a CAR of the present application having the same transmembrane domain as them.

The transmembrane domainmay comprise a costimulatory domain derived from CD28, 4-1BB, OX-40 or ICOS, which comprise a sequence shown as SEQ ID NO: 29 or SEQ ID NO: 31. For example, the costimulatory domain can be CD28, and the CAR can include CAR0043 or a CAR of the present application having the same costimulatory domain as CAR0043, wherein the sequence of the costimulatory domain is shown as. SEQ ID NO: 29. For another example, the costimulatory domain can be 4-1BB, and the CAR can include CAR0097, CAR0099 or a CAR having the same costimulatory domain as them, wherein the sequence of the costimulatory domain is shown as SEQ ID NO: 31.

The intracellular signal transduction domain of the CAR can include a signal transduction domain derived from CD3, with a sequence shown as SEQ ID NO: 37. For example, the CAR can include CAR0043, CAR0097, CAR0099 or a CAR of the present application having the same intracellular signal transduction domain as them.

The CAR can also comprise a hinge region that may be linked to the C terminal of the BCMA-binding domain and located at the N terminal of the transmembrane domain, and the hinge region has a sequence of SEQ ID NO: 25. For example, the CAR may comprise CAR0043, CAR0097, CAR0099 or a CAR of the present application having the same hinge region as them.

The CAR may also comprise an HA-tag that may be located at the N terminal of the BCMA-binding domain, and the HA-tag has a sequence of SEQ ID NO: SEQ ID NO: 5. For example, the CAR may comprise CAR0043 or a CAR of the present application having the same signal peptide as CAR0043.

The CAR may also be linked to a signal peptide that may be located at the N terminal of the CAR, and the signal peptide has a sequence of SEQ ID NO: 3. For example, the CAR may comprise CAR0043, CAR0097, CAR0099 or a CAR having the same signal peptide as them.

The CAR may be linked to a cleaving peptide, such as T2A, and the cleaving peptide may be located at the C terminal of the intracellular signal transduction domain, wherein the cleaving peptide has a sequence of SEQ ID NO: 35. For example, CAR0043 and CAR0099 may be linked to the cleaving peptide.

The CAR may also be linked to a marker detection signal that is located at the C terminal of the CAR, the marker detection signal may be selected from the group consisting of GFP, RFP and YFP, and the marker detection signal has a sequence of SEQ ID NO: 37. For example, the marker detection signal may be a GFP, and the CAR may include CAR0043 or a CAR of the present application having the same marker detection signal as CAR0043. The marker detection signal may also be an EGFRt marker detection signal, with a sequence shown as SEQ ID NO: 39. For example, CAR0099 may be linked to the marker detection signal.

For example, the CAR may comprise CAR0043, CAR0097, CAR0099 or a CAR of the present application having the same light chain variable region and heavy chain variable region as them.

For example, the CAR of the present application may be CAR0043, and the LCDRs 1-3 of CAR0043 comprise an amino acid sequence of SEQ ID NO: 17, SEQ ID NO: 18 and SEQ ID NO: 19 respectively; the VL comprises an amino acid sequence of SEQ ID NO: 15; the HCDRs 1-3 comprise an amino acid sequence of SEQ ID NO: 9, SEQ ID NO: 10 and SEQ ID NO: 11 respectively; the VH comprises an amino acid sequence of SEQ ID NO: 7; the C-peptide between the VH and the VL comprises a sequence of SEQ ID NO: 23; its hinge region comprises a sequence of SEQ ID NO: 25; its transmembrane domain comprises an amino acid sequence of SEQ ID NO: 27; its costimulatory domain is a CD28 costimulatory domain, with a sequence of SEQ ID NO: 29; its CD3ζ intracellular signal transduction domain comprises an amino acid sequence of SEQ ID NO: 33; the CAR0043 may also comprise a cleaving peptide of SEQ ID NO: 35 and a GFP marker detection signal of SEQ ID NO: 37; and the CAR0043 may also comprise a KOZAK sequence of SEQ ID NO: 1, a CD8a signal peptide of SEQ ID NO: 3, and an HA-tag of SEQ ID NO: 5.

For example, the CAR of the present application may be CAR0097, and the LCDRs 1-3 comprise an amino acid sequence of SEQ ID NO: 17, SEQ ID NO: 18 and SEQ ID NO: 19 respectively; the VL comprises an amino acid sequence of SEQ ID NO: 15; the HCDRs 1-3 comprise an amino acid sequence of SEQ ID NO: 9, SEQ ID NO: 10 and SEQ ID NO: 11 respectively; the VH comprises an amino acid sequence of SEQ ID NO: 7; the C-peptide between the VH and the VL comprises a sequence of SEQ ID NO: 23; its hinge region comprises a sequence of SEQ ID NO: 25; its transmembrane domain comprises a sequence of SEQ ID NO: 27; its costimulatory domain is a 4-1BB costimulatory domain of SEQ ID NO: 31; its CD3ζ intracellular signal transduction domain comprises a sequence of SEQ ID NO: 33; the CAR0097 may also comprise a KOZAK sequence of SEQ ID NO: 1 and a CD8a signal peptide of SEQ ID NO: 3.

For example, the CAR of the present application may be CAR0099, and the LCDRs 1-3 comprise an amino acid sequence of SEQ ID NO: 17, SEQ ID NO: 18 and SEQ ID NO: 19 respectively; the VL comprises an amino acid sequence of SEQ ID NO: 15; the HCDRs 1-3 comprises an amino acid sequence of SEQ ID NO: 9, SEQ ID NO: 10 and SEQ ID NO: 11 respectively; the VH comprises an amino acid sequence of SEQ ID NO: 7; the C-peptide between the VH and the VL comprises a sequence of SEQ ID NO: 23; its hinge region comprises a sequence of SEQ ID NO: 25; its transmembrane domain comprises a sequence of SEQ ID NO: 27; its costimulatory domain is a 4-1BB costimulatory domain of SEQ ID NO: 31; its CD3ζ intracellular signal transduction domain comprises a sequence of SEQ ID NO: 33; the CAR0099 may also comprise a cleaving peptide of SEQ ID NO: 35 and an EGFRt marker detection signal of SEQ ID NO: 39; and the CAR0099 may also comprise a KOZAK sequence of SEQ ID NO: 1 and a CD8a signal peptide of SEQ ID NO: 3.

The proteins, the polypeptides and/or the amino acid sequences involved in the present application should also be understood to at least include functional variants or homologues having the same or similar functions as the proteins or the polypeptides.

In the present application, the functional variants may be proteins or polypeptides which are obtained by substituting, deleting or adding one or more amino acids in the amino acid sequences of the above proteins and/or polypeptides (such as antibodies able to specifically bind with the BCMA or fragments thereof). For example, the functional variants can include proteins or polypeptides that have different amino acid sequences due to substitution, deletion and/or insertion of at least one amino acid, such as 1 to 30, 1 to 20 or 1 to 10, or such as 1, 2, 3, 4 or 5. The functional variants can substantially remain the biological characteristics of the proteins or the polypeptides that are unmodified (substitution, deletion or addition). For example, the functional variants can remain at least 60%, 70%, 80%, 90% or 100% of the biological activity (such as antigen binding ability) of the original proteins or polypeptides. For example, the substitution may be a conservative one.

In the present application, the homologues may be proteins or polypeptides that have at least about 85% (such as at least about 85%, 90%, 91%, 92%, 93%, 94%, 95%, 96%, 97%, 98%, 99% or higher) of amino acid sequence homology with the above proteins and/or polypeptides (such as antibodies able to specifically bind with the BCMA or fragments thereof).

In the present application, the homology generally refers to the likeness, similarity or correlation between two or more sequences. The "sequence homology percentage" can be calculated by the following method: two to-be-compared sequences being compared in a comparison window to determine the number of positions having the same nucleic acid base (such as A, T, C, G and I) or the same amino acid residues (such as Ala, Pro, Ser, Thr, Gly, Val, Leu, Ile, Phe, Tyr, Trp, Lys, Arg, His, Asp, Glu, Asn, Gln, Cys and Met) in the two sequences so that the number of matching positions is obtained; then the number of the matching positions being divided by the total number of positions in the comparison window (i.e. the window size); and the result being multiplied by 100 to obtain the sequence homology percentage. The comparison for determining the sequence homology percentage can be conducted by a variety of methods known in the art, for example, using publically available computer software such as BLAST, BLAST-2, ALIGN or Megalign (DNASTAR) software. Those skilled in the art can determine appropriate parameters for sequence comparison, including any algorithm needed for implementing maximum comparison within compared full-length sequence ranges or target sequence regions. The homology may also be determined by the following methods: FASTA and BLAST. The description of the FASTA algorithm can be found in "Improved Tools for Biological Sequence Comparison" by W. R. Pearson and D. J. Lipman, Proceedings of the National Academy of Sciences of the United States of America (Proc. Natl. Acad. Sci.), 85: 2444-2448, 1988; and "Rapid and Sensitive Protein Similarity Searches" by D. J. Lipman and W. R. Pearson, Science, 227: 1435-1441, 1989. The description of the BLAST algorithm could be found "A Basic Local Alignment Search Tool" by S. Altschul, W. Gish, W. Miller, E. W. Myers and D. Lipman, Journal of Molecular Biology, 215: 403-410, 1990.

Nucleic Acid, Vector, Cell, Preparation Method and Composition

In another aspect, the present application provides an isolated nucleic acid molecule, which may encode the CAR of the present application. The isolated nucleic acid molecule encoding the CAR of the present application may comprise a nucleotide sequence of SEQ ID NO: 50 or SEQ ID NO: 52 or functional variants thereof. The nucleic acid molecule of the present application may be isolated. For example, the nucleic acid molecule may be produced or synthesized by the following methods: (i) in-vitro amplification, such as polymerase chain reaction (PCR) amplification; (ii) cloning and recombination; (iii) purification, such as digestion and gel electrophoresis separation; or (iv) synthesis, such as chemical synthesis. In some embodiments, the isolated nucleic acid molecule is prepared by the recombinant DNA technology.

In another aspect, the present application provides a vector, which may contain the nucleic acid molecule. In the present application, the vector can be selected from one or more of a plasmid, a retroviral vector and a lentiviral vector. The lentiviral vector of the present application may comprise the CAR. For example, the lentiviral vector of the present application may comprise a nucleotide sequences of SEQ ID NO: 50 and/or SEQ ID NO: 52 or functional variants thereof. In addition, the vector can also contain other genes, for example, a marker gene allowing the vector to be selected in a suitable host cell and under an appropriate condition. In addition, the vector can also contain an expression control element that allows the coding region to be correctly expressed in a suitable host. Such a control element is well-known to those skilled in the art, and, for example, can include a promoter, a ribosome-binding site, an enhancer, and other control elements for regulating gene transcription or mRNA translation. In some embodiments, the expression control sequence is a regulable element. The specific structure of the expression control sequence can be varied according to the functions of species or cell types, but generally contains a 5' non-transcribed sequence and 5' and 3' non-translated sequences which participate in the transcription initiation and the translation initiation respectively, such as a TATA box, a capped sequence, a CAAT sequence, etc. For example, 5' non-transcribed expression control sequence can contain a promoter region, which can comprise a promoter sequence for transcribing and controlling functionally-linked nucleic acids. The one or more nucleic acid molecules of the present application can be operably linked to the expression control element. The vector can include, for example, plasmids, cosmids, viruses, bacteriophages or other vectors commonly used in, for example, genetic engineering. For example, the vector is an expression vector, including a vector scFv plasmid and/or a CAR plasmid.

In some embodiments, the virus-involved vector may be a lentiviral vector that may comprise vector scFv plasmids and/or CAR plasmids. For example, the virus may be a lentivirus LV0002, which may comprise a vector scFv plasmid PXLV0008 that may comprise a nucleic acid scFv0008 molecule, and/or a CAR plasmid PXLV0009 that may comprise a nucleic acid CAR0009 molecule. For example, the virus may be a lentivirus LV0011, which may comprise a vector scFv plasmid PXLV0008 that may comprise a nucleic acid scFv0008 molecule, and/or a CAR plasmid PXL0041 that may comprise a nucleic acid CAR0041 molecule. For example, the virus may be a lentivirus LV0013, which may a vector scFv plasmid PXL0032 that may include a nucleic acid scFv0032, and/or a CAR plasmid PXL0043 that may include a nucleic acid CAR0043. For example, the virus may be a lentivirus LV0022, which may comprise a vector scFv plasmid PXL0032 that may comprise a nucleic acid scFv0032, and/or a CAR plasmid PXL0097 that may comprise a nucleic acid CAR0097. For example, the virus may be a lentivirus LV0023, which may contain a vector scFv plasmid PXL0032 that may include a nucleic acid scFv0032, and/or a CAR plasmid PXL0099 that may include a nucleic acid CAR0099. In some embodiments, the virus-involved vector may also comprise retroviral vectors, which may comprise the scFv plasmids and/or the CAR plasmids. In some embodiments, the virus-involved vector may also comprise retroviral vectors, which may comprise the scFv plasmids and/or the CAR plasmids.

In the present application, the T lymphocyte may comprise thymocyte, natural T lymphocyte, immature T lymphocyte, mature T lymphocyte, resting T lymphocyte or activated T lymphocyte. The T cell may be a helper T cell (Th), such as a helper T cell 1 (Th1) or a helper T cell 2 (Th2). The T lymphocyte may be a $CD4^+$ helper T cell (HTL; $CD4^+$ T cell), a cytotoxic T cell (CTL; $CD8^+$ T cell), a tumor-infiltrating cytotoxic T cell (TIL; $CD8^+$ T cell), a $CD4^+/CD8^+$ T cell, a $CD4^-/CD8^-$ T cell or any other T lymphocyte subtypes. In some embodiments, the T lymphocyte may be a naive T cell ($T_N$ cell). In some embodiments, the T lymphocyte may be a central memory T cell ($T_{CM}$ cell). In some embodiments, the T lymphocyte may be an effector T cell ($T_{EM}$ cell). In some embodiments, the T lymphocyte may be a NK T cell. In the present application, the T lymphocyte may be derived from peripheral blood cells, umbilical cord blood cells and/or leukocytes.

In the present application, the T lymphocyte may be a $T_{CM}$ cell, which may have the characteristics of $CD45RO^+/CD62L^+$. The T lymphocyte may be a $T_{EM}$ cell, which may have the characteristics of $CD45RO^+/CD62L^-$. The T lymphocyte may be a $T_N$ cell, which may have the characteristics of $CD45RO^-/CD62L^+$. The T lymphocyte may be a NK T cell, which may be subdivided as $NK1.1^+$, $NK1.1^-$, $CD4^+$, $CD4^-$, $CD8^+$ and $CD8^-$. After activated, the NK T cell can produce a large number of interferon $-\gamma$, IL-4 (interleukin 4) and granulocyte-macrophage colony-stimulating factor. In addition, the NK T cell can also produce some cytokines and chemotactic factors (such as IL-2, IL-13, IL-17, IL-21 and tumor necrosis factor-$\alpha$). In another aspect, the present application provides an immune effector cell that can contain the CAR, the nucleic acid molecule or the vector of the present application. In the present application, the immune effector cell can be a mammalian cell. In the present application, the immune effector cell can be selected from a T lymphocyte and a natural killer (NK) cell.

In another aspect, the present application provides a method for preparing the immune effector cell, which may comprise introducing the vector of the present application into the immune effector cell. For example, the vector of the present application can be introduced into the immune effector cell, such as the T lymphocyte or the natural killer (NK) cell. In some embodiments, each type of or each cell may comprise one or one type of vector of the present application. In some embodiments, each type of or each cell may comprise multiple (such as two or more) or multiple types (such as two or more types) of vectors of the present application. For example, the vector of the present application can be introduced into the cell. For example, the immune effector cell can be transfected by the retroviral vector to integrate a viral genome carrying the CAR molecule into a host genome, ensuring the long-term, stable expression of a target gene. For another example, the transposon can be utilized to introduce a CAR-carrying plasmid (transposon) and a transposase-carrying plasmid into a target cell. For another example, the CAR molecule can be added into the genome by a gene editing method (such as CRISPR/Cas9). In the present application, the CAR molecule-carrying vector of the present application can be introduced into the cell by a method known in the art, such as electroporation, lipofectamine (lipofectamine 2000, Invitrogen), etc.

In another aspect, the present application provides a composition, which may comprise the immune effector cell and a pharmaceutically acceptable adjuvant.

The pharmaceutically acceptable adjuvants may comprise buffer, antioxidant, preservative, low-molecular weight polypeptide, protein, hydrophilic polymer, amino acid, sugar, chelating agent, counter-ion, metal complex and/or nonionic surfactant.

In the present application, the composition may be prepared for oral administration, intravenous administration (such as intravenous injection, I.V), intramuscular administration (such as intramuscular injection, I.M.), in-situ administration in a tumor site, inhalation, rectal administration, vaginal administration, transdermal administration or subcutaneous repository administration.

The composition of the present application may contain a therapeutically effective amount of the antibody or antigen-binding fragment thereof. The therapeutically effective amount is a dose required to prevent and/or treat (at least partially treat) a disease (such as cancer) and/or any complication thereof in a subject having that disease or a development risk therefor.

Pharmaceutical Use

In another aspect, the present application provides a use of the CAR, the nucleic acid molecule, the vector or the immune effector cell in the preparation of drugs, wherein the drugs are used to treat diseases or conditions associated with the expression of BCMA. In the present application, the diseases or conditions associated with the expression of BCMA may be cancers or malignant tumors. In some embodiments, the cancers or malignant tumors may be selected from plasmocyte malignancy diseases, such as multiple myeloma, and may also be selected from B-cell malignant diseases, such as Hodgkin's lymphoma and non-Hodgkin's lymphoma.

In another aspect, the present application provides the CAR, the nucleic acid molecule, the vector or the immune effector cell, treating diseases or conditions associated with the expression of BCMA.

In another aspect, the present application provides a method for treating diseases or conditions associated with the expression of BCMA, comprising administering the CAR, the nucleic acid molecule, the vector or the immune effector cell to a patent.

Without intending to be bound by any theory, the following examples are merely intended to illustrate the working modes of device, method, and system of the present application, rather than to limit the scope of the invention of the present application.

EXAMPLES

Example 1: Construction of Recombinant Lentiviral Vectors

The following sequences were first artificially synthesized: KOZAK (the nucleotide sequence SEQ ID NO: 2), CD8a signal peptide (nucleotide sequence the SEQ ID NO: 4), HA-tag (nucleotide sequence SEQ ID NO: 6), scFv0032 (the nucleotide sequence SEQ ID NO: 44), hinge region (the nucleotide sequence SEQ ID NO: 26), transmembrane domain (the nucleotide sequence SEQ ID NO: 28), CD28 costimulatory domain (the nucleotide sequence SEQ ID NO: 30), CD3 intracellular signal transduction domain (the nucleotide sequence SEQ ID NO: 34), T2A cleaving peptide (the nucleotide sequence SEQ ID NO: 36), GFP (the nucleotide sequence SEQ ID NO: 38), and EGFRt (the nucleotide sequence SEQ ID NO: 40).

Meanwhile, a scFv0008 molecule was constructed as a control, and f the scFv0008 molecule comprise an amino acid sequence of SEQ ID NO: 41 (see U.S. Pat. No. 9,034,324, SEQ ID NO: 3 and SEQ ID NO: 4).

The HA-tag was located at the N terminal of the CAR molecule, and directly linked to the CD8a signal peptide. When the CAR molecule was expressed on the surface of a cell, the HA-tag could serve as a tag for detecting the CAR molecule or enriching of the CAR-T cell. In addition, the GFP was located at the C terminal of the CAR molecule, and directly linked to the T2A cleaving peptide. CAR molecules and the GFP protein in equal amounts could be formed after the T2A cleaving (see Szymczak, et al., correction of multi-gene deficiency in vivo using a single self-cleaving 2A peptide-based retroviral vector. nature biotechnology, 2004. 22: p. 589). Therefore, the expression (as shown in FIG. 1B) of the CAR molecules could be indirectly evaluated by detecting the GFP signal. FIG. 1B specifically shows the detection process: a lentiviral particle (1) being introduced into a cell by the cell membrane fusion (2); the package being removed (3); then the reverse transcription (4) being performed; the integration (5), transcription (6) and translation (7) then being performed; and the cleaving (8) being performed by the T2A cleaving peptide. The transduction efficiency can be evaluated by the expression of the GFP (9), the binding efficiency of the scFv and BCMA protein can be studied by BCMA-Fc (10), and the anti-HA antibody can be used to assay the expression of the CAR and enrich the CAR-T cell for functionality analysis (11).

Besides by detecting the GFP protein, the expression of CAR molecules can also be determined by other methods. For example, an appropriate amount of biotinylated BCMA and PE streptavidin can be used to mark the CAR molecules so that the expression of the CAR molecules can be reflected by PE signals. For another example, an appropriate amount of biotinylated anti-HA monoclonal antibody (biotinylated anti-HA mAb) and PE streptavidin can be used to mark the CAR molecules for detection.

The scFv molecule-contained plasmids, the CAR molecule-contained plasmids and the lentiviruses corresponding thereto used in the present application are shown in Table 1.

TABLE 1

| Vector Types Corresponding to Lentiviruses | | | | |
|---|---|---|---|---|
| No. | scFv plasmid | scFv molecule | CAR plasmid | CAR molecule | Lentivirus |
| 1 | PXL0008 | scFv0008 | PXL0009 | CAR0009 | LV0002 |
| 2 | PXL0008 | scFv0008 | PXL0041 | CAR0041 | LV0011 |
| 3 | PXL0032 | scFv0032 | PXL0043 | CAR0043 | LV0013 |
| 4 | PXL0032 | scFv0032 | PXL0097 | CAR0097 | LV0022 |
| 5 | PXL0032 | scFv0032 | PXL0099 | CAR0099 | LV0023 |

The following CAR plasmids were prepared (see FIG. 1A).

A lentiviral vector PLVX-EF1alpha-IRES-Puro was double digested with NotI and MluI, and vector fragments were recovered. The candidate scFv plasmid PXL0032 (the nucleotide sequence: SEQ ID NO: 44) was amplified by PCR, and a NotI restriction enzyme cutting site (containing a protective base), a CD8a signal peptide, an HA-tag, a hinge region, a transmembrane domain, a CD28 costimulatory factor and a CD3 intracellular signal transduction domain were added to the 5' terminal in sequence by extension PCR for gene synthesis, and the PCR amplification was conducted; a T2A cleaving peptide and an eGFP were obtained from a plasmid pMy-BirA-T2A-eGFP by PCR amplification, with a MluI restriction enzyme cutting site and a protective base on the 3' terminal; and then a PCR fragment, with a NotI restriction enzyme cutting site at the 5' terminal and a MluI restriction enzyme cutting site at the 3' terminal, were obtained by overlap PCR, the obtained fragment was double digested with NotI and MluI, and was recovered. The CAR plasmid numbered as PXL0043 was constructed through T4 ligation (the nucleotide sequence of CAR0043 was shown as SEQ ID NO: 50).

The CAR plasmid numbered as PXL0097 was obtained by a similar method. A lentiviral vector PLVX-EF1alpha-IRES-Puro was double digested with NotI and MluI, and vector fragments were recovered. The candidate scFv plasmid PXL0032 was amplified by PCR, and an a NotI restriction enzyme cutting site (containing a protective base), a CD8a signal peptide, a hinge region, a transmembrane domain, a 4-1BB costimulatory factor (nucleotide sequence: SEQ ID NO: 32) and a CD3 intracellular signal transduction domain were added to the 5' terminal by extension PCR for gene synthesis, and the PCR amplification was performed; then a PCR fragment, with a NotI restriction enzyme cutting site at the 5' terminal and a MluI restriction enzyme cutting site at the 3' terminal, were obtained by overlap PCR, the obtained fragment was double digested with NotI and MluI, and was recovered. The CAR plasmid numbered as PXL0097 was constructed through T4 ligation (the nucleotide sequence of the CAR molecule portion of CAR0097 was shown as SEQ ID NO: 52).

The CAR plasmid numbered as PXL0099 was obtained by a similar method. A lentiviral vector PLVX-EF1alpha-IRES-Puro was double digested with NotI and MluI, and vector fragments were recovered. The candidate scFv plasmid PXL0032 was amplified by PCR, and an a NotI restriction enzyme cutting site (containing a protective base), a CD8a signal peptide, a hinge region, a transmembrane domain, a 4-1BB costimulatory factor (nucleotide sequence: SEQ ID NO: 32), a CD3 intracellular signal transduction domain, a T2A cleaving peptide and EGFRt (nucleotide sequence: SEQ ID NO: 40) were added to the 5' terminal by extension PCR for gene synthesis, and the PCR amplification was performed; then a PCR fragment, with a NotI restriction enzyme cutting site at the 5' terminal and a MluI restriction enzyme cutting site at the 3' terminal, were obtained by overlap PCR, the obtained fragment was double digested with NotI and MluI, and was recovered. The CAR plasmid numbered as PXL0099 was constructed through T4 ligation (the nucleotide sequence of the CAR molecule portion of CAR0099 was shown as SEQ ID NO: 52).

Meanwhile, a CAR plasmid containing the scFv plasmid PXLV0008 was constructed as a control.

The CAR plasmid numbered as PXL0041 was obtained through the same method (the nucleotide sequence of the CAR molecule portion of CAR0041 was shown as SEQ ID NO: 48). A lentiviral vector PLVX-EF1alpha-IRES-Puro was double digested with NotI and MluI, and vector fragments were recovered. The candidate scFv plasmid PXLV0008 (nucleotide sequence: SEQ ID NO: 42) was amplified by PCR, and a NotI restriction enzyme cutting site (containing a protective base), a CD8a signal peptide, an HA-tag, a hinge region, a transmembrane domain, a CD28 costimulatory factor and a CD3 intracellular signal transduction domain were added to the 5' terminal in sequence by extension PCR for gene synthesis, and the PCR amplification was conducted; a T2A cleaving peptide and an GFP were obtained from a plasmid pMy-BirA-T2A-eGFP by PCR amplification, with a MluI restriction enzyme cutting site and a protective base on the 3' terminal; and then a PCR fragment, with a NotI restriction enzyme cutting site at the 5' terminal and a MluI restriction enzyme cutting site at the 3' terminal, were obtained by overlap PCR, the obtained fragment was double digested with NotI and MluI, and was recovered. The CAR plasmid numbered as PXL0041 was constructed through T4 ligation (the CAR molecule portion of CAR0041 comprise a nucleotide sequence of SEQ ID NO: 48).

The CAR plasmid numbered as PXLV0009 was obtained by a similar method. A lentiviral vector PLVX-EF1alpha-IRES-Puro was double digested with NotI and MluI, and vector fragments were recovered. The candidate scFv plasmid PXLV0008 was amplified by PCR, and an a NotI restriction enzyme cutting site (containing a protective base), a CD8a signal peptide, a hinge region, a transmembrane domain, a CD28 costimulatory factor and a CD3ζ intracellular signal transduction domain were added to the 5' terminal by extension PCR for gene synthesis, and the PCR amplification was performed; then a PCR fragment, with a NotI restriction enzyme cutting site at the 5' terminal and a MluI restriction enzyme cutting site at the 3' terminal, were obtained by overlap PCR, the obtained fragment was double digested with NotI and MluI, and was recovered. The CAR plasmid numbered as PXLV0009 was constructed through T4 ligation (the nucleotide sequence of the CAR molecule portion of CAR0009 was shown as SEQ ID NO: 46).

Figure 2:
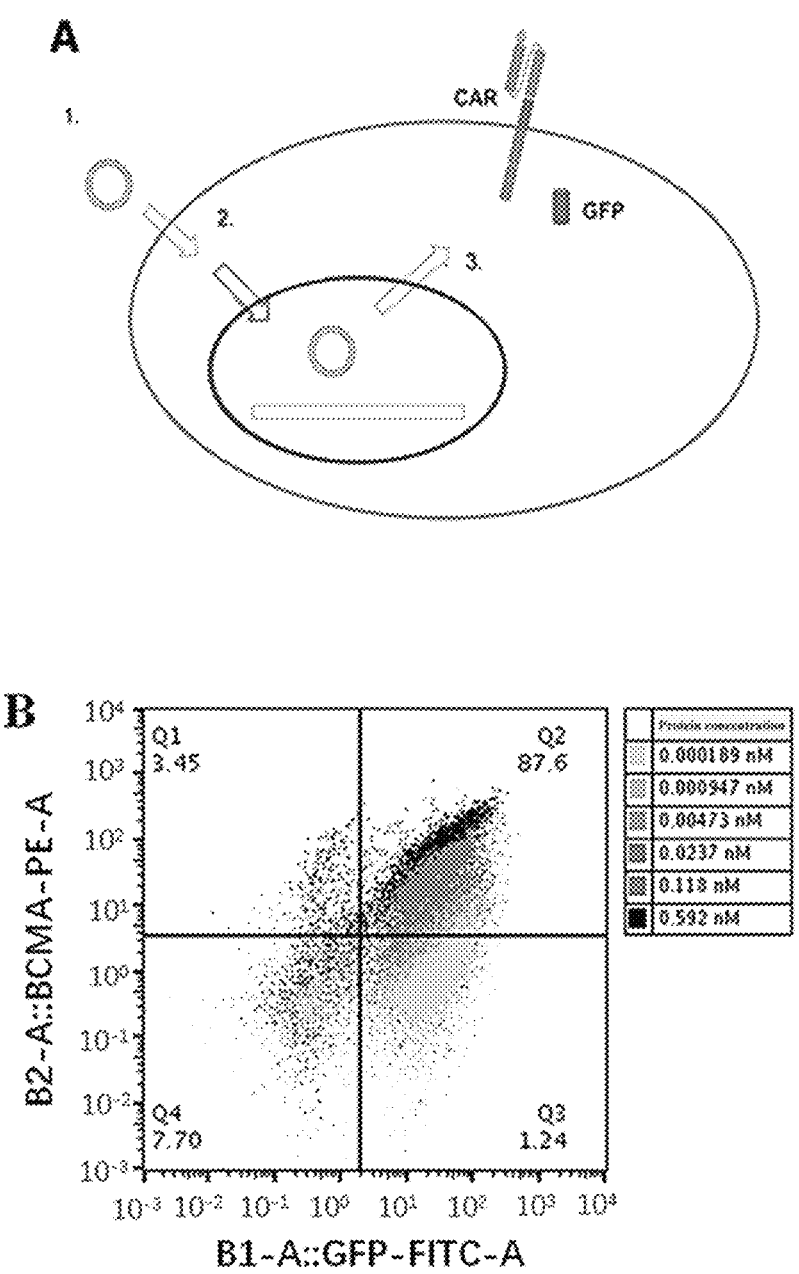
FIG. 2A shows a schematic diagram of the process of transiently transfecting T cells with CAR plasmids of the present application.
FIG. 2B shows the expression of CAR molecules in the T cells transiently transfected by the CAR plasmids of the present application.

Example 2: Expressions of CAR Molecules on Transiently-Transfected 293T Cell Samples As shown in FIG. 2A, the CAR plasmids PXLV0009, PXL0041 and PXL0043 prepared in example 1 were transiently transfected into 293T cells using PEI as a transfection reagent, so that a PXLV0009-293T cell, a PXL0041-293T cell and a PXL0043-293T cell were respectively obtained. 72 hours after transient transfection, the PXLV0009-293T cell, the PXL0041-293T cell and the PXL0043-293T cell were used to evaluate the expression capabilities of the candidate CAR molecules. In FIG. 2A, 1 represented a plasmid and a transfection reagent, 2 represented transient transfection, and 3 represented expression and T2A cleaving peptide cleaving.

The expressions of the CAR molecules were evaluated by utilizing the methods in example 1. Specifically, the dose of the biotinylated BCMA was changed by the gradient dilution for protein concentration in the presence of excessive PE streptavidin with a fixed concentration, so that the change of PE signals as shown in FIG. 2B was obtained. X axis represented GFP protein signals expressed in the cells, and Y axis represented PE signals obtained by the CAR molecules marked using the gradiently-diluted biotinylated BCMA and the fixed amount of PE streptavidin.

Figure 3:
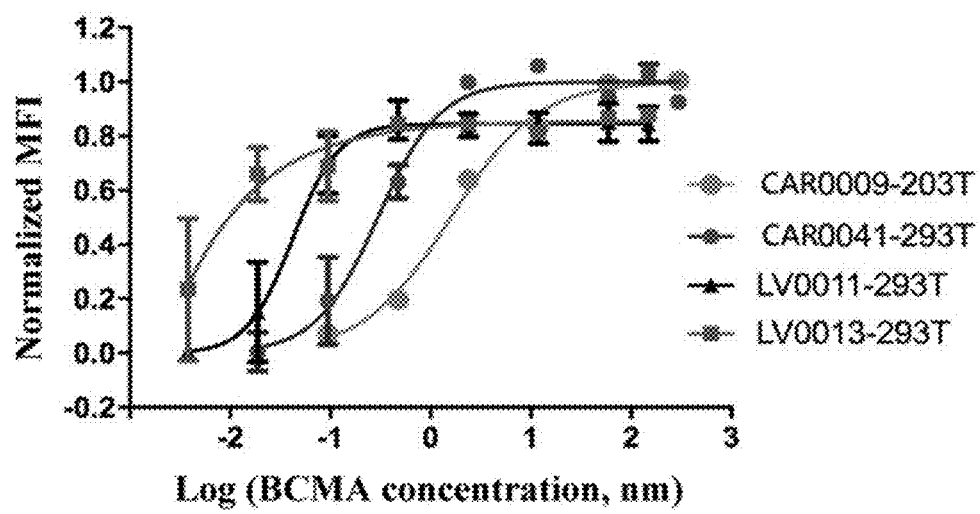
FIG. 3 shows the expression of CAR molecules in the T cells transiently transfected by the CAR plasmids of the present application.

The gradiently-diluted biotinylated BCMA protein (295.86 nM to 3.79 pM) was used to assay the 293T cells transiently transfected with the candidate CAR plasmids, so that a PE signal change curve (as shown in FIG. 3) was obtained. $EC_{50}$ values for the binding of BCMA proteins with CAR molecules on the surfaces of cells as measured by curve fitting, were as shown in Table 2.

TABLE 2

$EC_{50}$ Values for the Binding of BCMA Protein with CAR Molecules on Surfaces of Cells

| Sample | GFP % | Percentage of CAR marked with 500 ng of BCMA | CAR %:GFP % | $EC_{50}$ (nM) |
|---|---|---|---|---|
| PXL0009-293T | N/A | 18.0 | N/A | 1.59 |
| PXL0041-293T | 41.8 | 16.1 | 0.39 | 0.30 |
| PXL0043-293T | 32.3 | N/A | N/A | N/A |

Similarly, 72 hours after transient transfection of the 293T cell samples, the CAR molecules were marked using the biotinylated anti-HA monoclonal antibody (anti-HA mAb) and the PE streptavidin, and then GFP positive rates (GFP %), CAR positive rates (CAR %), and ratios of them were obtained by flow cytometry. The results were as shown in Table 3.

TABLE 3

Flow Cytometry Results for Expressions of CAR Molecules

| Sample | GFP % | Percentage of CAR marked with 500 ng of anti-HA mAb | CAR %:GFP % |
|---|---|---|---|
| PXL0009-293T | N/A | N/A | N/A |
| PXL0041-293T | 43.1 | 18.8 | 0.44 |
| PXL0043-293T | 32.25 | 29.4 | 0.91 |

It could be known from example 1 that PXLV0009 was a reference plasmid, and the CAR0009 molecule contained therein did not comprise a sequence encoding the GFP and the HA-tag. Therefore, no GFP signal for the PXLV0009 plasmid and no PE signal for the binding of a CAR with a biotinylated anti-HA monoclonal antibody (biotinylated anti-HA mAb) could be detected in the cell sample. Therefore, a PXLV0009-293T cell sample could be used as a negative control for flow cytometry. Different from PXL0043, PXL0041 and PXL0037 as reference plasmids could encode the GFP protein and the HA tag, so that GFP signals could be detected in a PXL0041-293T cell sample, and the binding (PE signal) of the CAR with the biotinylated BCMA protein or the biotinylated anti-HA monoclonal antibody (biotinylated anti-HA mAb) could also be detected respectively, therefore, PXL0041 and PXL0037 can serve as positive controls for flow cytometry.

The result showed that the GFP signal could be detected in a PXL0043-293T cell sample, and the binding (PE signal) of the CAR with the biotinylated anti-HA monoclonal antibody (biotinylated anti-HA mAb) could also be detected, which demonstrated that the CAR molecules encoded by the PXL0043 plasmid could be expressed on cells.

Example 3: Expressions of CAR Molecules on Lentivirus-Transduced 293T Cell Samples

3.1. Packaging of Lentiviruses

A shuttle plasmid was needed to achieve the simultaneous cotransfection of the CAR plasmids numbered as PXLV0009, PXL0041 and PXL0043 that were prepared in example 1 into 293T cells with other packaging plasmids, so that the lentiviruses were packaged in the cells. The specific steps were as follows.

Taking lentivirus packaging in 10 cm culture dishes as an example, the 293T cells were inoculated into DMEM medium containing 10% of FBS at a concentration of $6\times10^4$ cells/cm$^2$, and were cultured in the environment of 37° C., 5% $CO_2$ and saturated humidity for 3 days, and then the transfection was conducted. Before transfection, two EP tubes were prepared with 500 μl of opti-MEM in each EP tube, wherein, 3 μg of lentiviral helper vector PSPAX2, 2 pMD2.G and 5 μg of the vector prepared in example 1 (CAR plasmid numbered as PXLV0009, PXL0041 or PXL0043) were added to one tube and the mixture solution was thoroughly mixed, so that a tube containing plasmid was obtained; and 30 μl of PEI with a concentration of 1 mg/ml was added to the other tube and the mixture solution was thoroughly mixed. The solution containing PEI in the other tube was then added dropwise to the tube containing the plasmid while the obtained solution was thoroughly mixed, and 30 minutes after standing at room temperature, the resultant solution was uniformly added to the aforementioned 293T cells dropwise. 24 hours after transfection, 6 ml of DMEM medium containing 10% of FBS was replaced.

72 hours later, the supernatant was collected and added into a centrifuge tube, and then was centrifuged at 3000 g under 4° C. for 10 minutes, and the supernatant was ready for purification after filtered by a 0.45 μm filter.

The supernatant was centrifuged by an ultracentrifuge at 27000 g under 4° C. for 4 hours. The supernatant was removed, the precipitate was resuspended with 100 μl of pre-cooled PBS, and was resuspended overnight at 4° C. after no particle existing. Then the virus suspension was taken out and dispensed. Lentiviruses LV0011 (corresponding to the CAR plasmid PXL0041) and LV0013 (corresponding to the CAR plasmid LV0043) were obtained respectively.

3.2. Evaluation of Packaging Efficiencies of Lentiviruses

By detecting viral titers (biological titers) with transduction activities in the supernatant obtained in the process of lentiviral packaging, the packaging efficiencies of lentiviruses were evaluated. The specific assay steps were as follows.

293T cells were inoculated into a six-well plate in a quantity of $1\times10^5$ cells/well, and were cultured with 500 μl of DMEM medium containing 10% of FBS in the environment of 37° C., 5% $CO_2$ and saturated humidity. After the cells were cultured for 24 hours, lentiviral transduction was performed, and 100 μl, 50 μl, 25 μl and 12.5 μl of the supernatant were taken and added to six-well plates (two wells for each sample volume). The cells were then continued to be cultured in the environment of 37° C., 5% $CO_2$ and saturated humidity. 72 hours after the lentiviral transduction, the 293T cells were digested and resuspended for flow cytometry.

Figure 4:
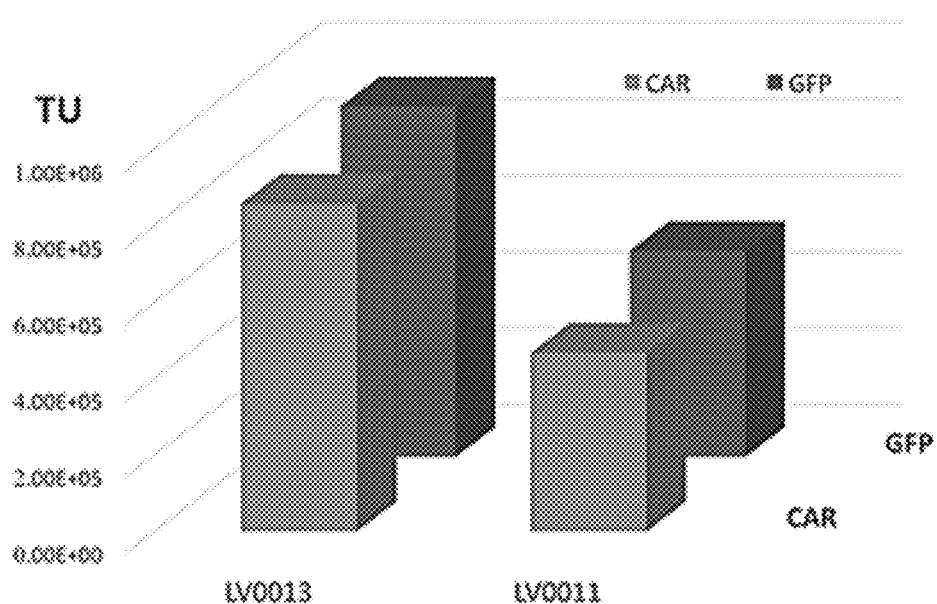
FIG. 4 shows results of a biological titer assay for the CAR plasmids of the present application packed with lentivirus.

As both the CAR molecular-encoding gene and the GFP protein-encoding gene were carried in LV0013, both the CAR molecule and the GFP protein could be expressed in 293T cells transduced with LV0013 at the same time. By detecting the GFP fluorescence signals in the 293T cells through the flow cytometry, the lentiviral biological titer (referred to as GFP titer) in the supernatant could be calculated:

biological titer(TU/ml)=(GFP positive rate×293T cell number)/virus sample volume Or, the LV00013-transduced 293T cells were marked with the biotinylated BCMA and the PE-streptavidin, and the CAR positive rate (referred to as CAR titer) was detected through the flow cytometry:

biological titer(TU/ml)=(CAR positive rate*293T cell number)/virus sample volume The biological titer assay result for the supernatant obtained in the aforementioned packaging process was shown in FIG. 4 and Table 4.

TABLE 4

Biological Titer Assay Result

| Sample | CAR titer (TU/ml) | GFP titer (TU/ml) |
|---|---|---|
| LV0011 | 4.68E+05 | 5.38E+05 |
| LV0013 | 8.58E+05 | 9.17E+05 |

Example 4: Preparation of CAR-T Cells

On day 1, about 65 ml of peripheral blood was collected from a healthy donor, Ficoll was used for separation to obtain PBMCs, and then CD3 MicroBeads was further used for sorting out T cells. The obtained T cells were further activated by CD3/CD28 Dynabeads. About 24 hours after the activation (on day 2), the lentiviruses LV0011 and LV0013 prepared in example 3 were added respectively for transduction (MOI=4), with a T cell concentration of about $1.5\times10^6$ cells/ml during the transduction. On day 3, the transduced T cells were supplemented with fresh medium once. Afterwards, counting was performed every day, and the cell concentration was kept between $(0.6\sim2.0)\times10^6$ cells/ml, and a growth curve of the cells was plotted.

On day 6 of the cell culture, a CAR positive rate (CAR %), a GFP positive rate (GFP %) and a CD4/CD8 ratio were detected by the flow cytometry. On day 10, the functions of CAR-T cells were evaluated in vitro.

According to the aforementioned process, LV0011-CAR-T cells and LV0013-CAR-T cells were obtained, and the T cells of the donor were adopted as a control. Table 5 summarizes the aforementioned preparation process for CAR-T cells.

TABLE 5

Preparation Process of CAR-T Cells

| Time | Event | Data |
|---|---|---|
| Day 1 | Collecting peripheral blood from a healthy donor | 65 ml |
| | Obtaining PBMCs by Ficoll separation | $2.05 \times 10^8$ cells |
| | Obtaining T cells by CD3 MicroBeads sorting | $9.16 \times 10^7$ cells |
| | Time for activation by CD3/CD28 Dynabeads | ~24 h |
| | CAR-T cell medium condition | CTS OpTmizer, 1% CTS Immune Cell SR, 50-200 IU/ml IL-2, 1% L-Glu |

TABLE 5-continued

Preparation Process of CAR-T Cells

Figure 10:
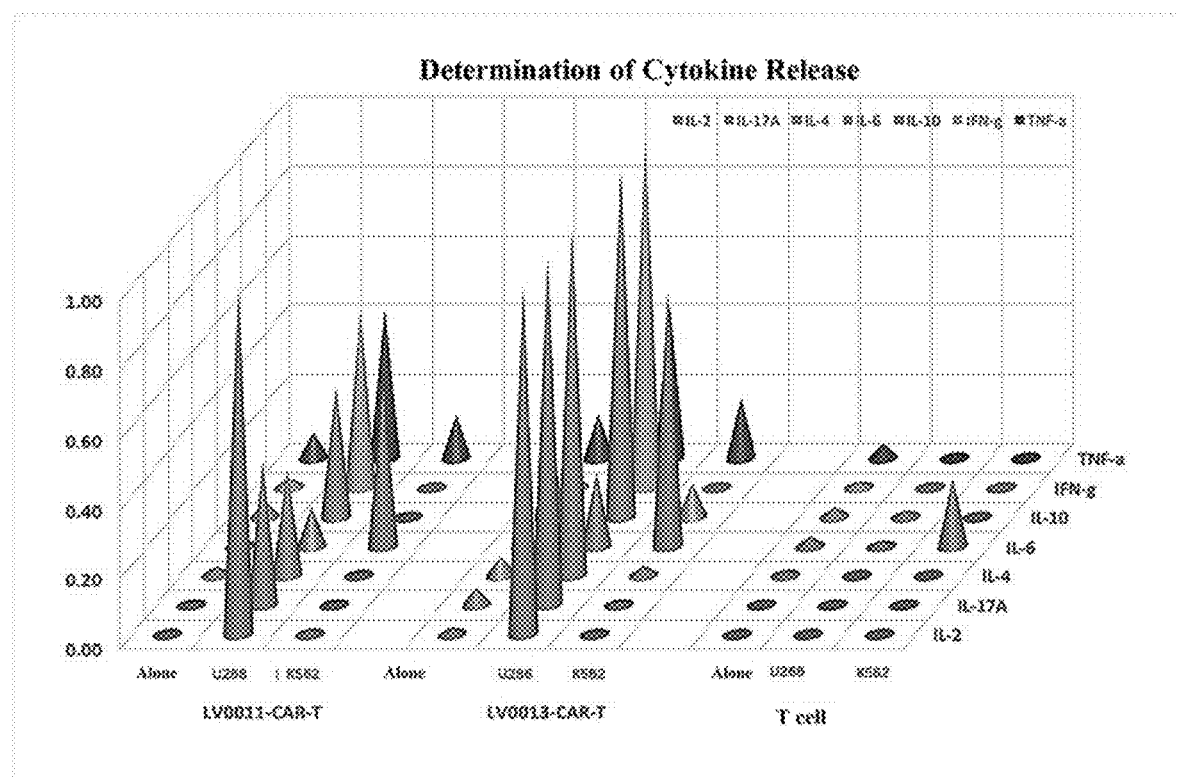
FIG. 10 shows results of cytokine-release assay obtained after the co-incubation of CAR-T cells of the present application with target cells.

| Time | Event | Data |
|---|---|---|
| Day 2 | Lentiviral transducting of T cells | MOI = 4, cell concentration = $1.49 \times 10^6$ cells/ml; except not adding lentiviruses, other operations for the T cell control group were the same as those for the CAR-T cell group. |
| Day 6 | Determinating of CAR positive rate | Data were shown in Table 6. |
| Day 10 | Testing CD 107a degranulation | Data were shown in Table 8 and FIG. 10. |

Figure 5:
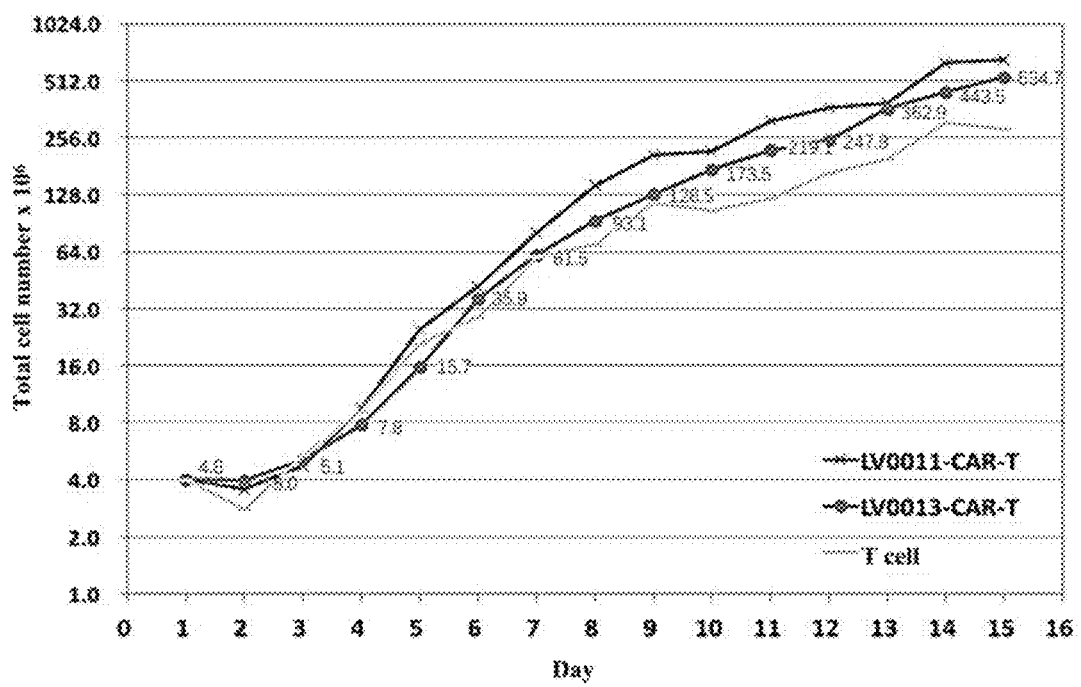
FIG. 5 shows the growth of the CAR-T cells of the present application.

Growth curves for the LV0011-CAR-T cell, the LV0013-CAR-T cell and the control T cell were as shown in FIG. 5. Data such as the CAR positive rates that were obtained by the flow cytometry on day 6 of the cell culture were as shown in Table 6.

TABLE 6

Result of CAR Positive Rate Assay by Flow Cytometry

| Sample | CAR % | CAR MFI | CD8 % | CAR % in CD4 | CAR % in CD8 |
|---|---|---|---|---|---|
| LV0011-CAR-T | 62.8 | 30.7 | 37.6 | 58.3 | 68.5 |
| LV0013-CAR-T | 58.3 | 41.3 | 47.9 | 55.8 | 60.8 |
| T cell | N/A | N/A | 29.6 | N/A | N/A |

Example 5: Data for the Binding of CAR Molecules with the BCMA Protein

Figure 6:
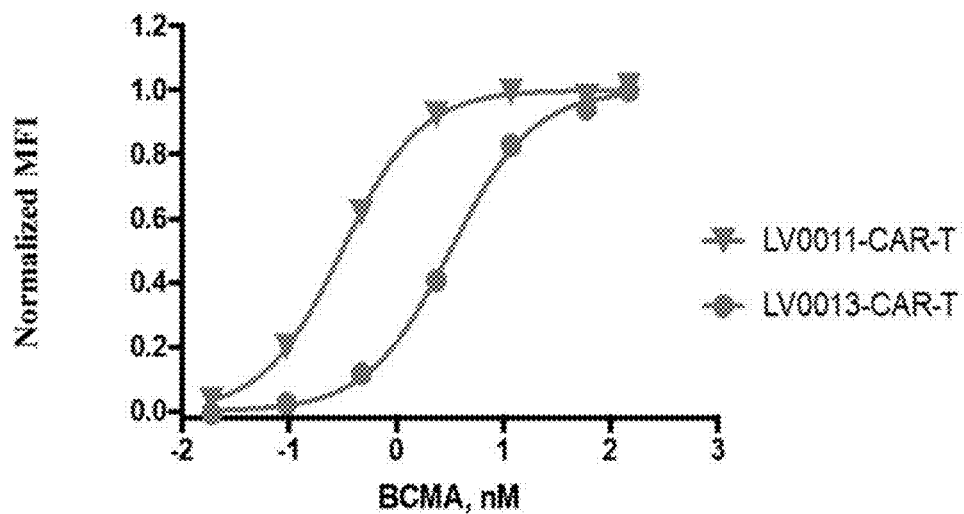
FIG. 6 shows results of the ability of the CAR molecules of the CAR-T cells of the present application to bind with BCMA.

Further, the capabilities of CAR molecules expressed on the CAR-Ts prepared in example 4 to bind with the BCMA protein were detected by using gradiently-diluted biotinylated BCMA protein to mark CAR molecules (identical with the method in example 2) in the presence of excessive PE streptavidin with a fixed concentration. The result was as shown in FIG. 6 and Table 7.

Example 7: Results for Binding of CAR Molecules with the BCMA Protein

| Sample | $EC_{50}$ |
|---|---|
| LV0011-CAR-T | 0.31 |
| LV0013-CAR-T | 3.19 |

According to the aforementioned data, the candidate CAR molecules expressed on the T cells could normally bind to the BCMA protein. However, there is a significant difference between determined $EC_{50}$ values for cell samples prepared in different batches. Such a difference may be caused by the different densities of the CAR molecules expressed on the surfaces of the cells due to the different cell types, sample preparation methods and batches.

Example 6: CD107a Degranulation Test

6.1. CD107a Degranulation Test

The biological potency of the CAR-T cells was evaluated in vitro by the CD107a Degranulation Test. CD107a is a marker for an intracellular microvesicle. When a microvesicle loaded with granzyme are fused with a cell membrane, the quantity of CD107a on the cell membrane is increased. Therefore, when the microvesicle recovery is blocked by using monesin (obtained from BioLegend), the intensity of microvesicle release can be quantitatively reflected. After the CAR-T is stimulated by a target antigen on a target cell, the granzyme is released. The activation of T cells can be determined by detecting the increase of CD107a through the flow cytometry.

Firstly, the CAR-T cells (LV00011-CAR-T cells or LV00013-CAR-T cells) obtained in example 4, together with target cells U266, monesin and a CD107a antibody were incubated for 3 to 6 hours, wherein the CAR-T cells and the target cells had the same cell concentration of $5 \times 10^5$ cells/ml. Then, after the sample was marked with CD8 and PD1 antibodies, the flow cytometry was performed. The CAR positive cells among the CAR-T cells were detected by detecting a coexpressed GFP, while CAR positive cells among LV00011-CAR-T cells as a control were marked by a biotinylated BCMA-Fc and PE streptavidin. In the test, the negative control was co-incubated with K562 cells and CAR-T cells, and a cocktail instead of target cells was used to activate the CAR-T cells in the positive control.

Figure 7:
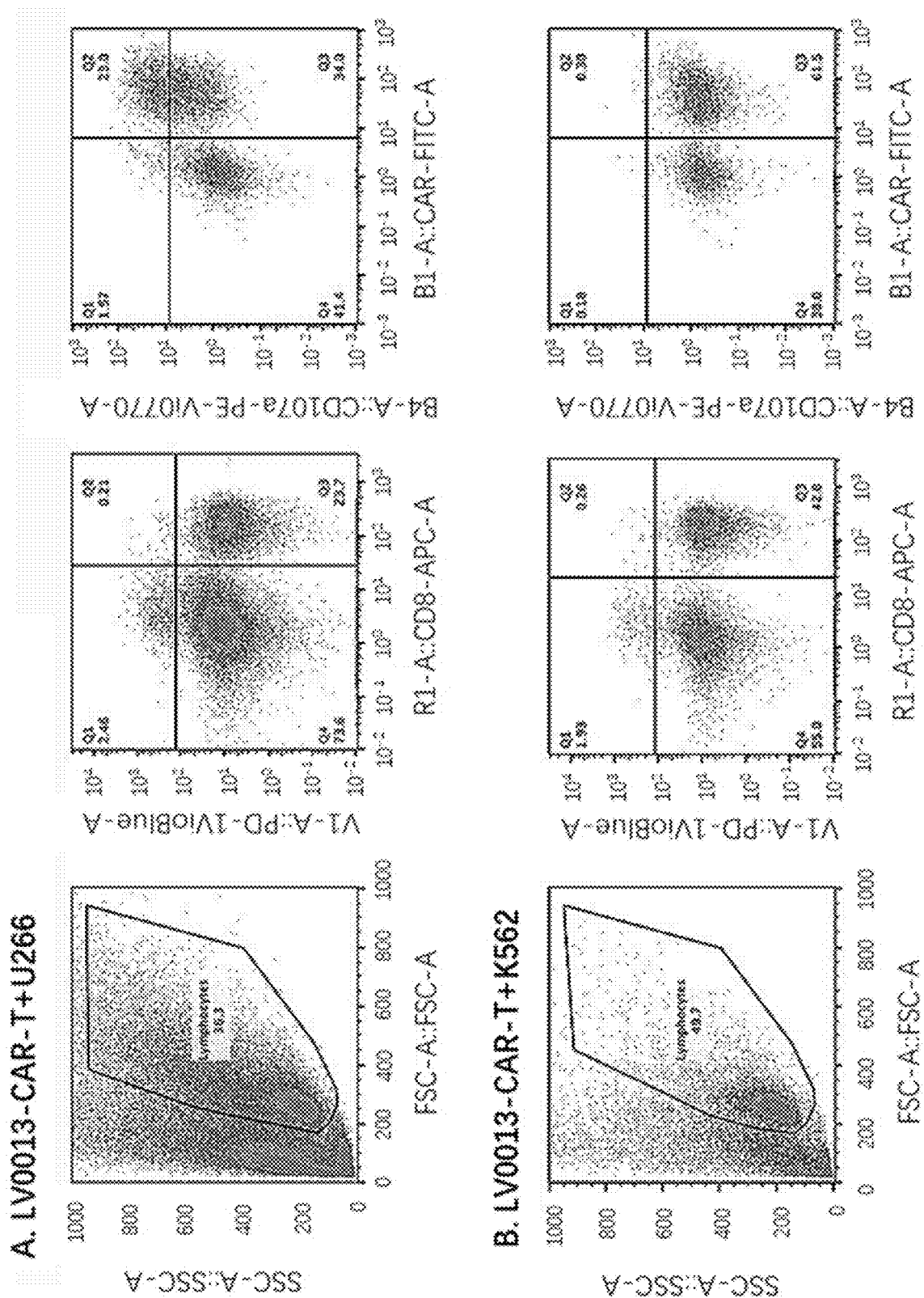
FIG. 7 shows results of FACS analysis of CD107a degranulation tests for the CAR-T cells of the present application.

Taking LV00013-CAR-T cells as an example, the flow cytometry result was as shown in FIG. 7.

For the cell sample in which LV00013-CAR-T and U266 were co-incubated, a P1 gate was selected on the FSC:SSC scatter plot, and cell debris at the lower left corner were removed; for cells in the P1 gate, CD8:PD1 could be further analyzed to obtain a CD8+/PD1− cell population (Q3); and in the CD8+/PD1− cell population, GFP: CD107a could be analyzed again to obtain the proportion of the CD107a-expressing cells in the CD8+/PD1−/CAR+ cell population (the CAR positive cell was marked by a coexpressed GFP signal) and the proportion of the CD107a-expressing cells in the CD8+/PD1−/CAR− cell population respectively.

For the cell sample in which LV00013-CAR-T and K562 were co-incubated, the cells were divided into population P1 and population P2 on the FSC: SSC scatter plot, wherein nearly no CD8 was expressed on the cells in population P2, which therefore might be K562 cells; for cells in the P1 gate, CD8: PD1 could be further analyzed; in the CD8+/PD1− cell population (Q3), GFP: CD107a could be analyzed again to obtain the proportion of the CD107a-expressing cells in each of CD8+/PD1−/CAR+ and CD8+/PD1−/CAR− as well.

6.2. CD107a Degranulation Test Data

According to the test operation in section 6.1 of example 6, the CAR-T cell samples (LV00011-CAR-T and LV00013-CAR-T cells) were co-incubated with target cells U266 (BCMA-positive) or K562 (BCMA-negative) respectively for 3 hours, and then the flow cytometry was performed. The CD107a degranulation test data results for cell samples are as shown in Table 8 and FIG. 8, and Table 8 and FIG. 8 both showed the ratios of the CD107a-expressing positive cells in the CD8+/PD1−/CAR+ cell subpopulation and the CD8+/PD1−/CAR− cell subpopulation.

TABLE 8

Ratios of CD107a-Expressing Positive Cells
in Different Cell Subpopulations

| Sample | CD8+/PD1−/CAR+ subpopulation | | CD8+/PD1−/CAR− subpopulation | |
|---|---|---|---|---|
| | K562 | U266 | K562 | U266 |
| LV0011-CAR-T | 2.01 | 10.70 | 2.71 | 3.33 |
| LV0013-CAR-T | 0.43 | 40.80 | 0.58 | 4.17 |
| T cell | N/A | N/A | 0.64 | 1.09 |

Figure 8:
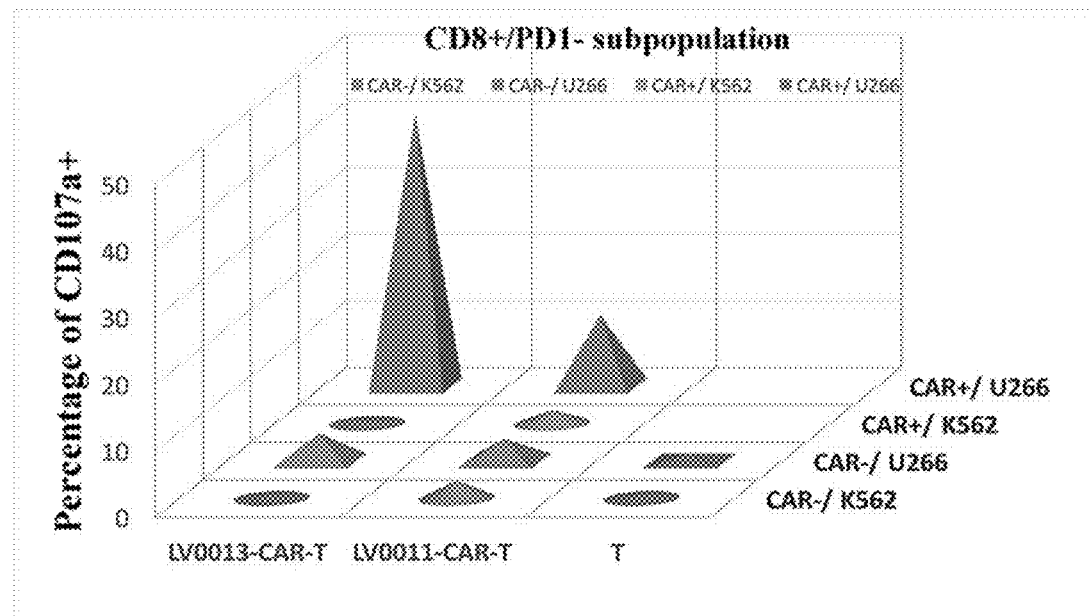
FIG. 8 shows results of CD107a degranulation test obtained after the incubation of CAR-T cells of the present application with different target cells.

As shown in FIG. 8 and FIG. 8, in the CAR-T sample co-incubated with U266, the CD107a value on the CD8+/PD1−/CAR+ cell subpopulation could reflect the situation where the CAR-T cells were specifically activated; while, in the CAR-T sample co-incubated with K562, the CD107a value on the CD8+/PD1−/CAR+ cell subpopulation could reflect the situation where the CAR-T cells were nonspecifically activated. By comparing the CD107a values on the CD8+/PD1−/CAR+ cell subpopulations from CAR-T samples co-incubated with U266, it could be concluded that the CD8+/PD1−/CAR+ subpopulation of LV00013-CAR-T cells could be specifically activated by the BCMA-positive cells (U266), and the activation for LV00013-CAR-T cells was stronger than that for LV00011-CAR-T cells as a control.

6.3. CD107a Degranulation Test Data Under a BCMA Protein Competition Condition

In addition, as the extracellular part of the BCMA protein expressed on the surface of a multiple myeloma (MM) cell can be cut by γ-secretase to form a soluble BCMA (sBCMA). The content of the soluble BCMA can be increased in a patient's serum, and its concentration is positively correlated with the malignant degree of a tumor. Therefore, when the CAR-T cells were co-incubated with target cells, 1 μg/ml of BCMA protein (BCMA-Fc fusion protein) was added to the medium to evaluate the effect of the soluble BCMA on CAR-T cell activation.

Figure 9:
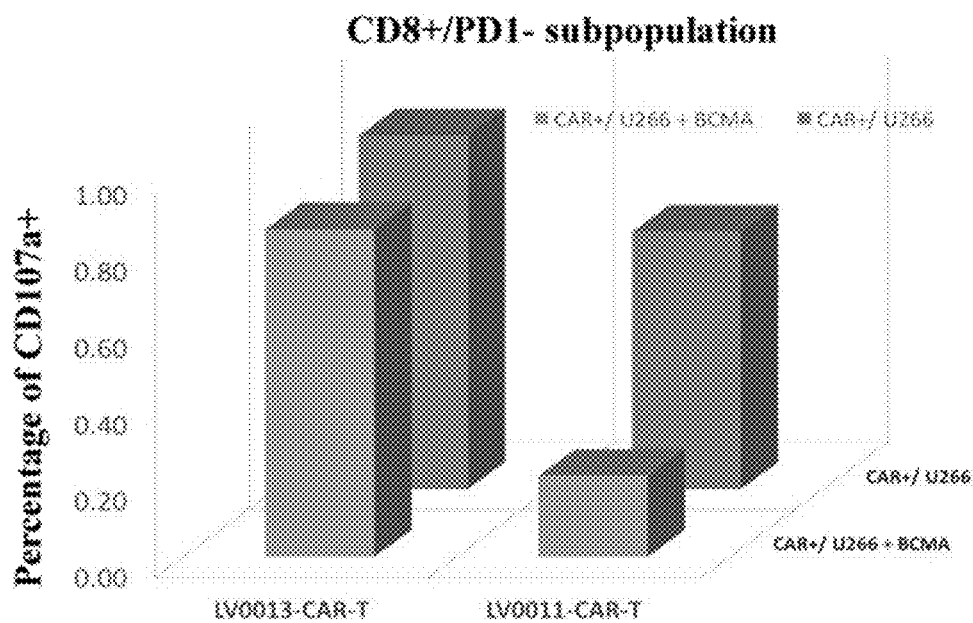
FIG. 9 shows results of CD107a degranulation test obtained after the incubation of CAR-T cells of the present application with different target cells under a BCMA protein competition condition.

A CD107a degranulation test result for the CAR-T cell samples under a BCMA protein competition condition was as shown in Table 9 and FIG. 9. As shown in FIG. 9, under the stimulation of the U266 cells, the effect of BCMA protein competition on the CD107a-positive cell ratio of the CD8+/PD1−/CAR+ subpopulation of the LV00013-CAR-T cell sample was minor, while the effect on the LV00011-CAR-T cell sample as a control was large.

TABLE 9

CD 107a Degranulation Test Data under
a BCMA Protein Competition Condition

| Sample | CD8+/PD1−/CAR+ subpopulation | | CD8+/PD1−/CAR− subpopulation | |
|---|---|---|---|---|
| | U266 and BCMA | U266 | U266 and BCMA | U266 |
| LV0011-CAR-T | 21.18 | 67.05 | 7.54 | 8.97 |
| LV0013-CAR-T | 85.47 | 92.20 | 12.39 | 15.92 |
| T cell | N/A | N/A | 0.00 | 8.58 |

Example 7: Determination of Cytokine Release

In a cytokine release determination experiment, after the to-be-determined CAR-T cells (5*10$^5$ cells, 100 μl) and target cells (5*10$^5$ cells, 100 μl) were co-incubated in RPMI-1640 medium for 24 hours, the cell culture supernatant was collected, and the secretions of IL-2, IL-4, IL-6, IL-10, IL-17A, TNF-α, IFN-γ and other factors were determined by the CBA method.

The assay result of cytokine release, obtained after a portion of the CAR-T cell samples cultured in the first batch were co-incubated with the target cells respectively, was as shown in Table 10 and FIG. 10. The release amount of a cytokine shown in FIG. 10 is a percentage relative to the detected maximum value in a sample. As shown in Table 10 and FIG. 10, the amounts of TNF-α, IFN-γ and IL-2 secreted by the LV00013-CAR-T cells stimulated by the BCMA-positive target cells U266 (+U266), were all greatly increased. The amounts of TNF-α, IFN-γ and IL-2 secreted by LV00013-CAR-T stimulated by the BCMA-negative K562 (+K562), were not increased.

TABLE 10

Determination Result of Cytokine Release

| Sample | IL-2 | IL-17A | IL-4 | IL-6 | IL-10 | IFN-γ | TNF-α |
|---|---|---|---|---|---|---|---|
| LV0011-CAR-T | 44.72 | 4.61 | 14.12 | 10.83 | 5.85 | 277.35 | 569.91 |
| LV0011-CAR-T + U226 | 8181.1 | 343.74 | 160.77 | 31.82 | 47.66 | 4847.04 | 3265.38 |
| LV0011-CAR-T + K562 | 117.31 | 4.1 | 3.04 | 126.72 | 0.45 | 4.25 | 942.7 |
| LV0013-CAR-T | 173.9 | 41.46 | 30.11 | 12.32 | 32.27 | 269.62 | 971.33 |
| LV0013-CAR-T + U226 | 8181.1 | 829.43 | 528.53 | 59.78 | 127.57 | 9516.08 | 3371.18 |
| LV0013-CAR-T + K562 | 41.99 | 8.32 | 14.6 | 205.06 | 12.47 | 13.74 | 1326.27 |
| T | 7.03 | N/A | 8.17 | 8.35 | 3.82 | 171.96 | 315.4 |
| T + U226 | N/A | N/A | N/A | 5.29 | 2.47 | 21.85 | 83.8 |
| T + K562 | N/A | N/A | N/A | 55.54 | N/A | N/A | 123.2 |

Example 8: Functions of CAR-T Cells from Different Donors

Figure 11:
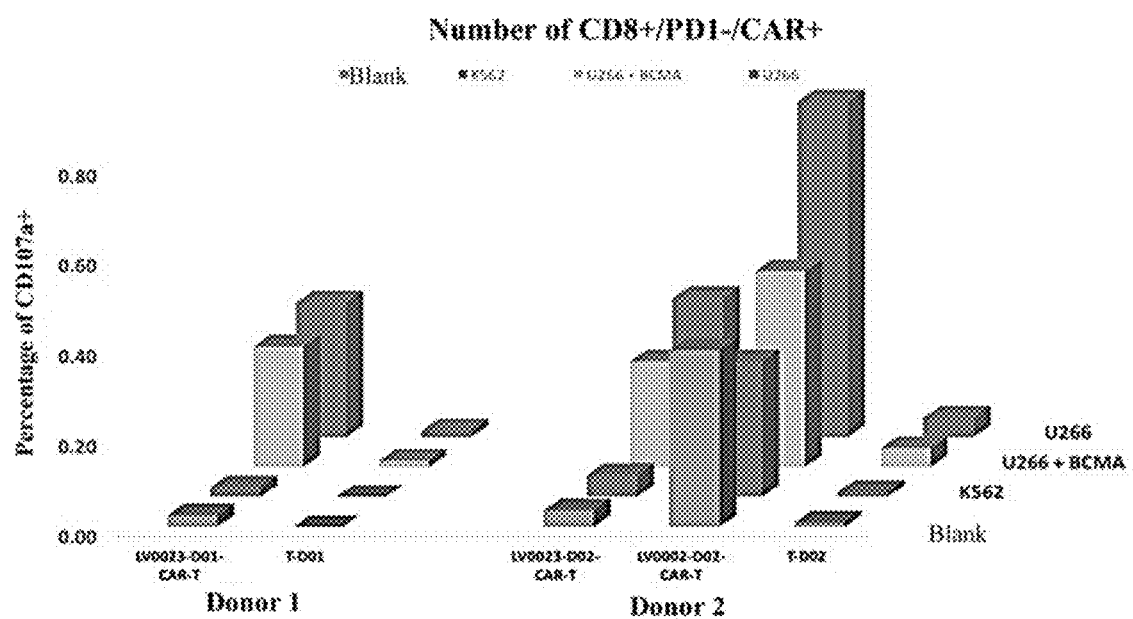
FIG. 11 shows results of function assay of CAR-T cells from different donors of the present application.

LV0002-CAR-T cells and LV0023-CAR-T cells were prepared by transducing the lentiviruses LV0002 and LV0023 prepared in example 3 into CAR-T cells with a experimental method similar to example 4, wherein, LV0023 viruses (corresponding to the CAR molecule encoded by the PXL0099 plasmid, with a costimulatory factor of 4-1BB) and LV0002 viruses (corresponding to the CAR molecule encoded by the PXLV0009 plasmid, with a costimulatory factor of CD28) were used to transduce T cells from different donors, for preparing CAR-T cells. T cells of donor 1 transduced with LV0002 viruses were named as LV0002-D01-CAR-T cells, T cells of donor 2 transduced with LV0002 viruses were named as LV0002-D02-CAR-T cells, T cells of donor 1 transduced with LV0023 viruses were named as LV0023-D01-CAR-T cells, and T cells of donor 2 transduced with LV0023 viruses were named as LV0023-D02-CAR-T cells. Meanwhile, T cells of donors themselves were adopted as controls, wherein, T cells coming from donor 1 were named as T cell-D01, and T cells coming from donor 2 were named as T cell-D02. The functions of these CAR-T cells were also assayed by using the CD107a degranulation test in example 6. The result is as shown in Table 11 and FIG. 11.

The data showed that the results for LV0023-CAR-T cells from two different donors were similar, that is, the LV0023-CAR-T cells of both donors could be specifically stimulated by the BCMA-positive U266 cells to produce CD107a, while the CD107a values generated under the stimulation of the BCMA-negative K562 cells were similar to the values generated under no stimulation (blank). The LV0002-CAR-T cells as a control could produce more CD107a under the stimulation of the U266 cells, which may resulted from the different scFvs and costimulatory factors for them. Moreover, the LV0002-CAR-T cells could have higher CD107a values under both the condition of no stimulation (blank) and the condition of K562 cell stimulation. In addition, the effect of a free BCMA protein on the capability of LV0023-CAR-T to produce CD107a was minor, while the effect of a free BCMA protein on the capability of LV0002-CAR-T to produce CD107a was large.

TABLE 11

Comparison of Functions of CAR-T Cells from Different Donors

| | | CD8+/PD1-/CAR+ subpopulation | | | |
|---|---|---|---|---|---|
| Donor | Sample | U266 | U266 and BCMA | K562 | Blank |
| Donor 1 | LV0023-D01-CAR-T | 29.7 | 26.7 | 2.19 | 2.60 |
| | T cell-D01 | 1.43 | 1.47 | 0.02 | 0.01 |
| Donor 2 | LV0023-D02-CAR-T | 30.7 | 23.4 | 4.92 | 3.70 |
| | LV0002-D02-CAR-T | 74.3 | 43.3 | 30.0 | 39.2 |
| | T cell-D01 | 4.29 | 4.24 | 1.15 | 1.01 |

Example 9: In-Vitro Experiment for Killing Effects of CAR-T on Target Cells

The CAR-T cells LV0023-D02-CAR-T from donor 2 prepared in example 8 were used for in-vitro killing function assay which was conducted by the calcein-AM fluorescence method. The specific steps of this assay were as follows. $5 \times 10^5$ BCMA-positive U266 cells and BCMA-negative K562 cells were respectively taken and resuspended in PBS+4% FBS solution, so that cell suspensions with concentrations of $1 \times 10^6$ cells/ml were prepared. The U266 cells and the K562 cells were respectively marked with 25 μM of calcein-AM. The marked U266 and K562 cells were respectively inoculated into U-bottom 96-well plates according to the quantity of 5000 cells per well; the to-be-assayed CAR-T cells or T cells as a control were then respectively added to the corresponding wells according to the three effector cell/target cell ratios of 50:1, 25:1 and 5:1 (E:T value), and the solution volume in each well was 200 μl. In addition, a PBS solution, in place of the effector cells, was added to the U266 or K562 cells, serving as a negative control for assay; and a cell lysis solution, in place of the effector cells, was added to the U266 or K562 cells, serving as a positive control for assay. Then, the U-bottom 96-well plates were incubated in the dark at 37° C. for 3 hours, and the supernatant solution was pipetted (with no cells being pipetted) from each well for fluorescence assay (excitation wavelength: 485/20 nm; emission wavelength: 530/25 nm). The relative proportion of the target cells (U266 or K562) which were killed by the effector cells and lysed to release calcein-AM can be calculated by the following formula:

$$\text{dissolution proportion } (\%) = \frac{F_{test} - F_{spont.}}{F_{max.} - F_{spont.}}$$

wherein, $F_{test}$ is an average fluorescence value for the replicate wells containing the target cells and the to-be-assayed T/CAR-T cells, $F_{spont.}$ is an average fluorescence value for the replicate wells containing the target cells and PBS, and $F_{max.}$ is an average fluorescence value for the replicate wells containing the target cells and the lysis solution.

Figure 12:
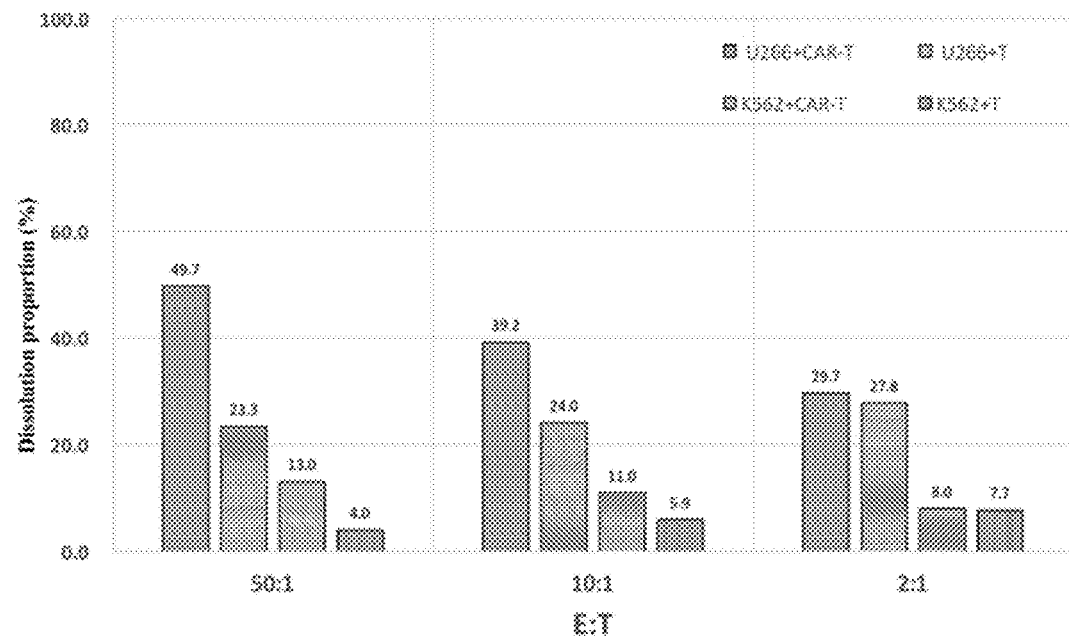
FIG. 12 shows in-vitro killing effects of CAR-T cells of the present application against target cells.

Taking the LV0023-D02-CAR-T sample as an example, the in-vitro killing effect of the CAR-T cells against the target cells was as shown in FIG. 12. The CAR-T cells had a strong killing effect against the BCMA-positive U266 cells, and the killing effect was enhanced as the E:T value increased, showing that a higher proportion of U266 cells were lysed to release calcein-AM. As a contrast, the CAR-T cells had a poor killing effect against the BCMA-negative K562 cells. In addition, the T cells had a certain degree of nonspecific killing effect against the U266 cells, and the nonspecific killing effect would not be changed as the E:T value increased. Therefore, the CAR-T cells had a remarkable BCMA-specific killing effect.

Example 10: Assay for Tumor Suppression in Tumor-Bearing Animal Models

Figure 13:
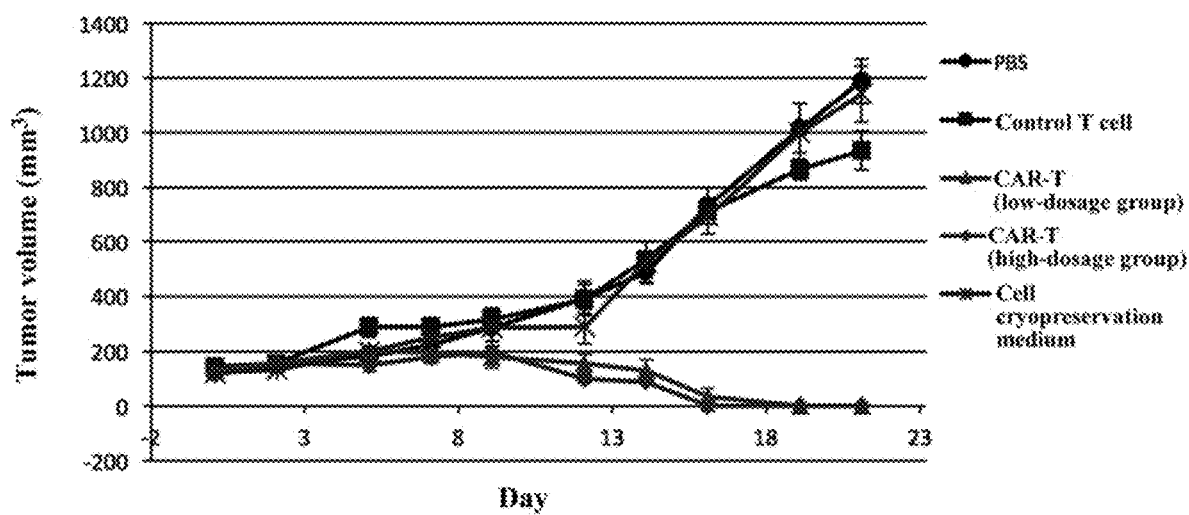
FIG. 13 shows results of animal model experiment for the tumor-killing effects of CAR-T cells of the present application.

The CAR-T cells (LV0023-D02-CAR-T) coming from donor 2 which were prepared in example 8 were used for an animal model experiment. Meanwhile, T cells coming from donor 2 (T cell-D02) were adopted as control T cells. Proliferating U266 cells were subcutaneously injected into immunodeficient NSG mice in a quantity of $2 \times 10^6$ cells per mouse, creating a U266 subcutaneous tumor-bearing model. When the tumor sizes reached 100-150 mm³, the tumor-bearing mice were divided into five groups according to Table 12, and the CAR-T cells (LV0023-D02-CAR-T), the control T cells (T cell-D02), PBS or cell cryopreservation medium containing 7.5% of DMSO, 23% of human serum albumin, 32.5% of compound electrolyte solution, 35% of glucose injection and 2% of normal saline) were injected into the tumor-bearing mice respectively. The cell cryopreservation medium of the present application contains 7.5% of DMSO, 23% of human serum albumin, 32.5% of compound electrolyte solution, 35% of glucose injection and 2% of normal saline. The mice were continuously fed, and the tumor sizes, the mouse weights and the survival states of the mice were recorded. The result was as shown in FIG. 13. The result of the mouse model experiment indicated that the high-dosage group and the low-dosage group both showed a good tumor-killing effect after a single injection of the CAR-T cells, and that 19 days after the injection, the tumors completely disappeared. On the contrary, the tumors in the mice for which the control T cells, PBS or the cell cryopreservation medium were injected continued to grow.

TABLE 12

| | | Grouping Solution for Animal Model Experiment | | | |
|---|---|---|---|---|---|
| Group | Number | CAR-T information | Administration method | Administration Dosage | Frequency of administration |
| 1 | 5 | PBS control | I.V. | 100 μl | single administration |
| 2 | 5 | Control T cell | I.V. | $10 \times 10^6$ cells/animal | single administration |
| 3 | 5 | CAR-T cell (low-dosage group) | I.V. | $2 \times 10^6$ cells/animal | single administration |
| 4 | 5 | CAR-T cell (high-dosage group) | I.V. | $10 \times 10^6$ cells/animal | single administration |
| 5 | 5 | Cell cryopreservation medium | I.V. | 100 μl | single administration |

The aforementioned detailed description is provided in an explanatory and illustrative manner rather than intended to limit the scope of the appended claims. So far, a variety of variations of the embodiments illustrated in the present application are apparent to those of ordinary skill in the art, and are kept within the scope of the appended claims and equivalent embodiments thereof.

What is claimed is:

1. A chimeric antigen receptor (CAR), wherein the CAR comprises a B-cell maturation antigen (BCMA)-binding domain, a transmembrane domain, a costimulatory domain and an intracellular signal transduction domain, the BCMA-binding domain comprises an antibody or a fragment thereof capable of specifically binding a BCMA protein, wherein the antibody or the fragment, comprises a heavy chain complementary determining region 1 (HCDR1), a heavy chain complementary determining region 2 (HCDR2) and a heavy chain complementary determining region 3 (HCDR3), wherein the HCDR1 comprises the amino acid sequence as set forth in SEQ ID NO: 9, the HCDR2 comprises the amino acid sequence as set forth in SEQ ID NO: 10, and the HCDR3 comprises the amino acid sequence as set forth in SEQ ID NO: 11, and wherein the antibody or the fragment, comprises a light chain complementary determining region 1 (LCDR1), a light chain complementary determining region 2 (LCDR2) and a light chain complementary determining region 3 (LCDR3), and wherein the LCDR1 comprises the amino acid sequence as set forth in SEQ ID NO: 17, the LCDR2 comprises the amino acid sequence as set forth in SEQ ID NO: 18, and the LCDR3 comprises the amino acid sequence as set forth in SEQ ID NO: 19.

2. The CAR of claim 1, wherein the antibody comprises a heavy chain variable region, and the heavy chain variable region comprises the amino acid sequence as set forth in SEQ ID NO: 7.

3. The CAR of claim 1, wherein the antibody comprises a light chain variable region, and the light chain variable region comprises the amino acid sequence as set forth in SEQ ID NO: 15.

4. The CAR of claim 1, wherein the antibody is a single-chain antibody fragment.

5. The CAR of claim 1, wherein the antibody comprises the amino acid sequence shown as SEQ ID NO: 43.

6. The CAR of claim 1, wherein the transmembrane domain comprises a transmembrane domain derived from a protein selected from a group consisting of α, β or ζ chain of the T cell receptor, CD28, CD3e, CD45, CD4, CD5, CD8a, CD9, CD16, CD22, CD33, CD37, CD64, CD80, CD86, CD134, CD137 and CD154.

7. The CAR of claim 1, wherein the transmembrane domain comprises the amino acid sequence as set forth in SEQ ID NO: 27.

8. The CAR of claim 1, wherein the costimulatory domain comprises a costimulatory domain derived from a protein selected from a group consisting of CD28, 4-1BB, OX-40 and ICOS.

9. The CAR of claim 1, wherein the costimulatory domain comprises the amino acid sequence as set forth in SEQ ID NO: 29 or SEQ ID NO: 31.

10. The CAR of claim 1, wherein the intracellular signal transduction domain comprises a signal transduction domain derived from CD3ζ.

11. The CAR of claim 1, wherein the intracellular signal transduction domain comprises the amino acid sequence as set forth in SEQ ID NO: 33.

12. The CAR of claim 1, wherein the CAR further comprises a hinge region linking the BCMA-binding domain to the transmembrane domain.

13. The CAR of claim 12, wherein the hinge region comprises the amino acid sequence as set forth in SEQ ID NO: 25.

14. The CAR of claim 1, wherein the CAR is further linked to a signal peptide.

15. The CAR of claim 14, wherein the signal peptide comprises the amino acid sequence as set forth in SEQ ID NO: 3.

16. The CAR of claim 1, wherein the CAR is further linked to a cleaving peptide.

17. The CAR of claim 16, wherein the cleaving peptide comprises an amino acid sequence derived from a T2A peptide.

18. The CAR of claim 16, wherein the cleaving peptide comprises the amino acid sequence as set forth in SEQ ID NO: 35.

19. The CAR of claim 1, comprising the amino acid sequence as set forth in SEQ ID NO: 49 or SEQ ID NO: 51.

20. An isolated nucleic acid molecule, encoding the CAR of claim 1.

21. An isolated nucleic acid molecule encoding CAR, comprising the nucleotide sequence as set forth in SEQ ID NO: 50 or SEQ ID NO: 52.

22. A vector, comprising the nucleic acid molecule of claim 20.

23. The vector of claim 22, wherein the vector is selected from a plasmid, a retroviral vector and a lentiviral vector.

24. An immune effector cell, comprising the CAR of claim 1.

25. The cell of claim 24, wherein the immune effector cell is selected from a T lymphocyte and a natural killer (NK) cell.

26. A method of preparing an immune effector cell, comprising introducing the vector of claim 22 into the immune effector cell.

27. A composition, comprising the immune effector cell of claim 24.

28. A method for treating a mammalian subject having a plasmocyte malignant disease or a B-cell malignant disease, the method comprises administering to said mammalian subject an effective amount of the immune effector cell of claim 24.

29. The method of claim 28, wherein the plasmocyte malignant disease is multiple myeloma.

30. The method of claim 28, wherein the B-cell malignant disease is Hodgkin's lymphoma or non-Hodgkin's lymphoma.

\* \* \* \* \*

SEQUENCE LISTING

<160> NUMBER OF SEQ ID NOS: 52

<210> SEQ ID NO 1
<211> LENGTH: 3
<212> TYPE: PRT
<213> ORGANISM: Artificial Sequence
<220> FEATURE:
<223> OTHER INFORMATION: KOZAK

<400> SEQUENCE: 1

Ala Ala Thr
1

<210> SEQ ID NO 2
<211> LENGTH: 9
<212> TYPE: DNA
<213> ORGANISM: Artificial Sequence
<220> FEATURE:
<223> OTHER INFORMATION: KOZAK (nucleotide)

<400> SEQUENCE: 2 gccgccacc                                                              9

<210> SEQ ID NO 3
<211> LENGTH: 21
<212> TYPE: PRT
<213> ORGANISM: Artificial Sequence
<220> FEATURE:
<223> OTHER INFORMATION: CD8a signal peptide

<400> SEQUENCE: 3

Met Ala Leu Pro Val Thr Ala Leu Leu Leu Pro Leu Ala Leu Leu Leu
1               5                   10                  15

His Ala Ala Arg Pro
            20

<210> SEQ ID NO 4
<211> LENGTH: 63
<212> TYPE: DNA

<213> ORGANISM: Artificial Sequence
<220> FEATURE:
<223> OTHER INFORMATION: CD8a signal peptide(nucleotide)

<400> SEQUENCE: 4
atggccctgc tgtgacagc tctgctcctc cctctggccc tgctgctcca tgccgccaga    60
ccc                                                                 63

<210> SEQ ID NO 5
<211> LENGTH: 9
<212> TYPE: PRT
<213> ORGANISM: Artificial Sequence
<220> FEATURE:
<223> OTHER INFORMATION: HA-tag

<400> SEQUENCE: 5

Tyr Pro Tyr Asp Val Pro Asp Tyr Ala
1               5

<210> SEQ ID NO 6
<211> LENGTH: 27
<212> TYPE: DNA
<213> ORGANISM: Artificial Sequence
<220> FEATURE:
<223> OTHER INFORMATION: HA-tag(nucleotide)

<400> SEQUENCE: 6
tacccatacg atgttccaga ttacgct                                       27

<210> SEQ ID NO 7
<211> LENGTH: 124
<212> TYPE: PRT
<213> ORGANISM: Artificial Sequence
<220> FEATURE:
<223> OTHER INFORMATION: VH

<400> SEQUENCE: 7

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Ser Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Arg Arg Asp Ser Phe Gly Ser Ile Ala Phe Asp
            100                 105                 110

Ile Trp Gly Gln Gly Thr Met Val Thr Val Ser Ser
        115                 120

<210> SEQ ID NO 8
<211> LENGTH: 372
<212> TYPE: DNA
<213> ORGANISM: Artificial Sequence
<220> FEATURE:
<223> OTHER INFORMATION: VH(nucleotide)

<400> SEQUENCE: 8

```
gaagtgcagc tggtggagtc tgggggaggc ttggtacagc ctggcaggtc cctgagactc      60
tcctgtgcag cctctggatt cacctttgat gattatgcca tgcactgggt ccggcaagct    120
ccagggaagg gcctggagtg ggtctcaggt attagttgga gtagtggtag cataggctat    180
gcggactctg tgaagggccg attcaccatc tccagagaca cgccaagaa ctccctgtat     240 ctgcaaatga acagtctgag agctgaggac acggcggtgt actactgcgc caaggactcc    300
cctagaaggg acagcttcgg aagcatagca ttcgacatat ggggtcaggg tacaatggtc    360
accgtcagct ca                                                        372
```

<210> SEQ ID NO 9
<211> LENGTH: 8
<212> TYPE: PRT
<213> ORGANISM: Artificial Sequence
<220> FEATURE:
<223> OTHER INFORMATION: HCDR1

<400> SEQUENCE: 9

```
Gly Phe Thr Phe Asp Asp Tyr Ala
1               5
```

<210> SEQ ID NO 10
<211> LENGTH: 8
<212> TYPE: PRT
<213> ORGANISM: Artificial Sequence
<220> FEATURE:
<223> OTHER INFORMATION: HCDR2

<400> SEQUENCE: 10

```
Ile Ser Trp Ser Ser Gly Ser Ile
1               5
```

<210> SEQ ID NO 11
<211> LENGTH: 17
<212> TYPE: PRT
<213> ORGANISM: Artificial Sequence
<220> FEATURE:
<223> OTHER INFORMATION: HCDR3

<400> SEQUENCE: 11

```
Ala Lys Asp Ser Pro Arg Arg Asp Ser Phe Gly Ser Ile Ala Phe Asp
1               5                   10                  15

Ile
```

<210> SEQ ID NO 12
<211> LENGTH: 24
<212> TYPE: DNA
<213> ORGANISM: Artificial Sequence
<220> FEATURE:
<223> OTHER INFORMATION: HCDR1(nucleotide)

<400> SEQUENCE: 12

```
ggattcacct ttgatgatta tgcc                                            24
```

<210> SEQ ID NO 13
<211> LENGTH: 24
<212> TYPE: DNA
<213> ORGANISM: Artificial Sequence
<220> FEATURE:
<223> OTHER INFORMATION: HCDR2(nucleotide)

<400> SEQUENCE: 13

```
attagttgga gtagtggtag cata                                            24
```

```
<210> SEQ ID NO 14
<211> LENGTH: 51
<212> TYPE: DNA
<213> ORGANISM: Artificial Sequence
<220> FEATURE:
<223> OTHER INFORMATION: HCDR3(nucleotide)

<400> SEQUENCE: 14
gccaaggact cccctagaag ggacagcttc ggaagcatag cattcgacat a          51

<210> SEQ ID NO 15
<211> LENGTH: 107
<212> TYPE: PRT
<213> ORGANISM: Artificial Sequence
<220> FEATURE:
<223> OTHER INFORMATION: VL

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ala Ser Ala Leu Pro Leu
                85                  90                  95

Thr Phe Gly Gly Gly Thr Lys Val Glu Ile Lys
            100                 105

<210> SEQ ID NO 16
<211> LENGTH: 321
<212> TYPE: DNA
<213> ORGANISM: Artificial Sequence
<220> FEATURE:
<223> OTHER INFORMATION: VL(nucleotide)

<400> SEQUENCE: 16
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaaa gggccactgg catcccagcc   180
aggttcagtg gcagtgggtc tgggacagac ttcactctca ccatcagcag cctagagcct   240
gaagattttg cagtttatta ctgtcagcag gccagtgccc tccctctcac ttttggcgga   300
gggaccaagg ttgagatcaa a                                             321

<210> SEQ ID NO 17
<211> LENGTH: 6
<212> TYPE: PRT
<213> ORGANISM: Artificial Sequence
<220> FEATURE:
<223> OTHER INFORMATION: LCDR1

<400> SEQUENCE: 17

Gln Ser Val Ser Ser Tyr
1               5
```

```
<210> SEQ ID NO 18
<211> LENGTH: 3
<212> TYPE: PRT
<213> ORGANISM: Artificial Sequence
<220> FEATURE:
<223> OTHER INFORMATION: LCDR2

<400> SEQUENCE: 18

Asp Ala Ser
1

<210> SEQ ID NO 19
<211> LENGTH: 9
<212> TYPE: PRT
<213> ORGANISM: Artificial Sequence
<220> FEATURE:
<223> OTHER INFORMATION: LCDR3

<400> SEQUENCE: 19

Gln Gln Ala Ser Ala Leu Pro Leu Thr
1               5

<210> SEQ ID NO 20
<211> LENGTH: 18
<212> TYPE: DNA
<213> ORGANISM: Artificial Sequence
<220> FEATURE:
<223> OTHER INFORMATION: LCDR1(nucleotide)

<400> SEQUENCE: 20
cagagtgtta gcagctac                                                 18

<210> SEQ ID NO 21
<211> LENGTH: 9
<212> TYPE: DNA
<213> ORGANISM: Artificial Sequence
<220> FEATURE:
<223> OTHER INFORMATION: LCDR2(nucleotide)

<400> SEQUENCE: 21 gatgcatcc                                                            9

<210> SEQ ID NO 22
<211> LENGTH: 27
<212> TYPE: DNA
<213> ORGANISM: Artificial Sequence
<220> FEATURE:
<223> OTHER INFORMATION: LCDR3(nucleotide)

<400> SEQUENCE: 22
cagcaggcca gtgccctccc tctcact                                       27

<210> SEQ ID NO 23
<211> LENGTH: 18
<212> TYPE: PRT
<213> ORGANISM: Artificial Sequence
<220> FEATURE:
<223> OTHER INFORMATION: Linker (VL-VH)

<400> SEQUENCE: 23

Gly Ser Thr Ser Gly Ser Gly Lys Pro Gly Ser Gly Glu Gly Ser Thr
1               5                   10                  15

Lys Gly

<210> SEQ ID NO 24
<211> LENGTH: 54
```

```
<212> TYPE: DNA
<213> ORGANISM: Artificial Sequence
<220> FEATURE:
<223> OTHER INFORMATION: Linker (VL-VH)(nucleotide)

<400> SEQUENCE: 24
ggcagcacca gcggctccgg caagcctggc tctggcgagg gcagcacaaa ggga            54

<210> SEQ ID NO 25
<211> LENGTH: 55
<212> TYPE: PRT
<213> ORGANISM: Artificial Sequence
<220> FEATURE:
<223> OTHER INFORMATION: Structural domain

<400> SEQUENCE: 25

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55

<210> SEQ ID NO 26
<211> LENGTH: 165
<212> TYPE: DNA
<213> ORGANISM: Artificial Sequence
<220> FEATURE:
<223> OTHER INFORMATION: Structural domain(nucleotide)

<400> SEQUENCE: 26
ttcgtgcccg tgttcctgcc cgccaaacct accaccaccc ctgcccctag acctcccacc      60
ccagccccaa caatcgccag ccagcctctg tctctgcggc cgaagcctg tagacctgct     120 gccggcggag ccgtgcacac cagaggcctg gacttcgcct gcgac                    165

<210> SEQ ID NO 27
<211> LENGTH: 21
<212> TYPE: PRT
<213> ORGANISM: Artificial Sequence
<220> FEATURE:
<223> OTHER INFORMATION: CD8a transmembrane domain

<400> SEQUENCE: 27

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 28
<211> LENGTH: 63
<212> TYPE: DNA
<213> ORGANISM: Artificial Sequence
<220> FEATURE:
<223> OTHER INFORMATION: CD8a transmembrane domain(nucleotide)

<400> SEQUENCE: 28
atctacatct gggcccctct ggccggcacc tgtggcgtgc tgctgctgag cctggtgatc      60
acc                                                                   63

<210> SEQ ID NO 29
```

<211> LENGTH: 41
<212> TYPE: PRT
<213> ORGANISM: Artificial Sequence
<220> FEATURE:
<223> OTHER INFORMATION: CD28 costimulatory domain

<400> SEQUENCE: 29

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 30
<211> LENGTH: 123
<212> TYPE: DNA
<213> ORGANISM: Artificial Sequence
<220> FEATURE:
<223> OTHER INFORMATION: CD28 costimulatory domain(nucleotide)

<400> SEQUENCE: 30
agaagcaagc ggagccggct gctgcacagc gactacatga acatgacccc aagacggcct     60
ggccccaccc ggaagcacta ccagccttac gcccctccca gagacttcgc cgcctaccgg    120
tcc                                                                  123

<210> SEQ ID NO 31
<211> LENGTH: 42
<212> TYPE: PRT
<213> ORGANISM: Artificial Sequence
<220> FEATURE:
<223> OTHER INFORMATION: 4-1BB costimulatory domain

<400> SEQUENCE: 31

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 32
<211> LENGTH: 126
<212> TYPE: DNA
<213> ORGANISM: Artificial Sequence
<220> FEATURE:
<223> OTHER INFORMATION: 4-1BB costimulatory domain(nucleotide)

<400> SEQUENCE: 32
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                               126

<210> SEQ ID NO 33
<211> LENGTH: 112
<212> TYPE: PRT
<213> ORGANISM: Artificial Sequence
<220> FEATURE:
<223> OTHER INFORMATION: CD3 intracellular signal transduction domain

<400> SEQUENCE: 33

Arg Val Lys Phe Ser Arg Ser Ala Asp Ala Pro Ala Tyr Gln Gln Gly

```
         1               5                  10                 15
      Gln Asn Gln Leu Tyr Asn Glu Leu Asn Leu Gly Arg Arg Glu Glu Tyr
                          20                   25                  30

Asp Val Leu Asp Lys Arg Arg Gly Arg Asp Pro Glu Met Gly Gly Lys
                     35                  40                  45

Pro Arg Arg Lys Asn Pro Gln Glu Gly Leu Tyr Asn Glu Leu Gln Lys
                50                  55                  60

Asp Lys Met Ala Glu Ala Tyr Ser Glu Ile Gly Met Lys Gly Glu Arg
       65                  70                  75                  80

Arg Arg Gly Lys Gly His Asp Gly Leu Tyr Gln Gly Leu Ser Thr Ala
                          85                  90                  95

Thr Lys Asp Thr Tyr Asp Ala Leu His Met Gln Ala Leu Pro Pro Arg
                     100                 105                 110

<210> SEQ ID NO 34
<211> LENGTH: 336
<212> TYPE: DNA
<213> ORGANISM: Artificial Sequence
<220> FEATURE:
<223> OTHER INFORMATION: CD3 intracellular signal transduction domain
      (nucleotide)

<400> SEQUENCE: 34
agagtgaagt tcagcagatc cgccgacgcc cctgcctacc agcagggaca gaaccagctg      60
tacaacgagc tgaacctggg cagacgggaa gagtacgacg tgctggacaa gcggagaggc     120
cgggaccccg agatgggcgg aaagcccaga cggaagaacc cccaggaagg cctgtataac     180
gaactgcaga agacaagat ggccgaggcc tacagcgaga tcggcatgaa gggcgagcgg      240
aggcgcggca gggccacga tggcctgtac cagggcctga gcaccgccac caaggacacc     300
tacgacgccc tgcacatgca ggccctgccc cccaga                               336

<210> SEQ ID NO 35
<211> LENGTH: 18
<212> TYPE: PRT
<213> ORGANISM: Artificial Sequence
<220> FEATURE:
<223> OTHER INFORMATION: cleaving peptide T2A

<400> SEQUENCE: 35

Glu Gly Arg Gly Ser Leu Leu Thr Cys Gly Asp Val Glu Glu Asn Pro
  1               5                  10                  15

Gly Pro

<210> SEQ ID NO 36
<211> LENGTH: 54
<212> TYPE: DNA
<213> ORGANISM: Artificial Sequence
<220> FEATURE:
<223> OTHER INFORMATION: cleaving peptide T2A(nucleotide)

<400> SEQUENCE: 36
gagggcagag gaagtcttct aacatgcggt gacgtggagg agaatcccgg ccct            54

<210> SEQ ID NO 37
<211> LENGTH: 239
<212> TYPE: PRT
<213> ORGANISM: Artificial Sequence
<220> FEATURE:
<223> OTHER INFORMATION: GFP

<400> SEQUENCE: 37
```

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 38
<211> LENGTH: 720
<212> TYPE: DNA
<213> ORGANISM: Artificial Sequence
<220> FEATURE:
<223> OTHER INFORMATION: GFP(nucleotide)

<400> SEQUENCE: 38
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 39
<211> LENGTH: 357
<212> TYPE: PRT
<213> ORGANISM: Artificial Sequence
<220> FEATURE:
<223> OTHER INFORMATION: EGFRt

<400> SEQUENCE: 39

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
 50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
            355
```

<210> SEQ ID NO 40
<211> LENGTH: 1071
<212> TYPE: DNA
<213> ORGANISM: Artificial Sequence
<220> FEATURE:
<223> OTHER INFORMATION: EGFRt(nucleotide)

<400> SEQUENCE: 40

```
atgctgctgc tcgtgacctc tttactgtta tgtgagctgc ccacccccgc tttttactg      60
atccctcgta aggtgtgtaa cggaatcggc attggcgagt tcaaggactc tttaagcatc    120
aacgccacaa acatcaagca cttcaagaat tgtacctcca tcagcggcga tttacacatt    180
ctccccgtgg cttttcgtgg cgattccttc acccacaccc ccctctggac ccccaagag     240
ctggacattt taaaaaccgt gaaggagatc accggctttc tgctgatcca agcttggccc    300
gagaatcgta ccgacctcca cgccttcgag aatttagaga ttattcgtgg aaggaccaag    360
cagcacggcc agttctcttt agccgtcgtg tctttaaaca ttaccagcct cggtttaagg    420
tctttaaagg agattagcga cggcgacgtg atcatctccg caacaagaa cctctgctac     480
gccaacacca tcaactggaa gaagctgttc ggaaccagcg ccaaaagac caagatcatc     540
agcaatcgtg agagaactc ttgtaaggcc actggtcaag tttgccacgc cctctgtagc     600
cccgaaggat gttggggccc cgagcctagg gactgtgtta gctgcagaaa cgtgagcaga    660
ggcagagagt gtgtggacaa atgcaattta ctggaaggag agcctaggga gttcgtggag    720
aacagcgaat gtatccagtg ccaccccgag tgtttacctc aagccatgaa catcacttgt    780
accggaaggg gccccgataa ctgcatccaa tgcgcccact acatcgacgg accccactgc    840
gtgaaaactt gtcccgccgg agtgatggga gagaataaca ctttagtgtg aagtacgcc     900
gacgctggcc acgtctgcca tctgtgccac cccaactgta cctacggctg cactggtccc    960
ggtttagagg gatgtcctac caacggcccc aagatcccct ccatcgccac cggaatggtg   1020
ggcgctctgt tattactgct ggtggtggct ctgggcatcg gtttattcat g            1071
```

<210> SEQ ID NO 41
<211> LENGTH: 246
<212> TYPE: PRT
<213> ORGANISM: Artificial Sequence
<220> FEATURE:
<223> OTHER INFORMATION: scFv0008

<400> SEQUENCE: 41

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Gly
            100                 105                 110

Ser Thr Ser Gly Ser Gly Lys Pro Gly Ser Gly Glu Gly Ser Thr Lys 115                 120                 125
Gly Gln Ile Gln Leu Val Gln Ser Gly Pro Glu Leu Lys Lys Pro Gly
            130                 135                 140

Glu Thr Val Lys Ile Ser Cys Lys Ala Ser Gly Tyr Thr Phe Thr Asp
145                 150                 155                 160

Tyr Ser Ile Asn Trp Val Lys Arg Ala Pro Gly Lys Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Glu Thr Ser Ala Ser Thr Ala
        195                 200                 205

Tyr Leu Gln Ile Asn Asn Leu Lys Tyr Glu Asp Thr Ala Thr Tyr Phe
    210                 215                 220

Cys Ala Leu Asp Tyr Ser Tyr Ala Met Asp Tyr Trp Gly Gln Gly Thr
225                 230                 235                 240

Ser Val Thr Val Ser Ser
            245

<210> SEQ ID NO 42
<211> LENGTH: 738
<212> TYPE: DNA
<213> ORGANISM: Artificial Sequence
<220> FEATURE:
<223> OTHER INFORMATION: scFv0008(nucleotide)

<400> SEQUENCE: 42
gacatcgtgc tgacccagag ccccccccagc ctggccatgt ctctgggcaa gagagccacc      60
atcagctgcc gggccagcga gagcgtgacc atcctgggca gccacctgat ccactggtat     120
cagcagaagc ccggccagcc ccccacccctg ctgatccagc tcgccagcaa tgtgcagacc     180
ggcgtgcccg ccagattcag cggcagcggc agcagaaccg acttcaccct gaccatcgac     240
cccgtggaag aggacgacgt ggccgtgtac tactgcctgc agagccggac catccccgg     300 acctttggcg gaggcaccaa actggaaatc aagggcagca ccagcggctc cggcaagcct     360
ggctctggcg agggcagcac aaagggacag attcagctgg tgcagagcgg ccctgagctg     420
aagaaacccg gcgagacagt gaagatcagc tgcaaggcct ccggctacac cttcaccgac     480
tacagcatca ctgggtgaa agagcccct ggcaagggcc tgaagtggat gggctggatc      540
aacaccgaga caagagagcc cgcctacgcc tacgacttcc ggggcagatt cgccttcagc     600
ctggaaacca gcgccagcac cgcctacctg cagatcaaca acctgaagta cgaggacacc     660
gccacctact tttgcgccct ggactacagc tacgccatgg actactgggg ccagggcacc     720
agcgtgaccg tgtccagc                                                   738

<210> SEQ ID NO 43
<211> LENGTH: 248
<212> TYPE: PRT
<213> ORGANISM: Artificial Sequence
<220> FEATURE:
<223> OTHER INFORMATION: scFv0032

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile

```
                35                  40                  45
Tyr Asp Ala Ser Lys Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ala Ser Ala Leu Pro Leu
                 85                  90                  95

Thr Phe Gly Gly Gly Thr Lys Val Glu Ile Lys Gly Ser Thr Ser Gly
                100                 105                 110

Ser Gly Lys Pro Gly Ser Gly Glu Ser Thr Lys Gly Glu Val Gln
            115                 120                 125

Leu Val Glu Ser Gly Gly Gly Leu Val Gln Pro Gly Arg Ser Leu Arg
130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Ser Ser Gly Ser Ile Gly Tyr Ala Asp Ser Val Lys Gly Arg
                180                 185                 190

Phe Thr Ile Ser Arg Asp Asn Ala Lys Asn Ser Leu Tyr Leu Gln Met
            195                 200                 205

Asn Ser Leu Arg Ala Glu Asp Thr Ala Val Tyr Tyr Cys Ala Lys Asp
210                 215                 220

Ser Pro Arg Arg Asp Ser Phe Gly Ser Ile Ala Phe Asp Ile Trp Gly
225                 230                 235                 240

Gln Gly Thr Met Val Thr Val Ser
                245

<210> SEQ ID NO 44
<211> LENGTH: 747
<212> TYPE: DNA
<213> ORGANISM: Artificial Sequence
<220> FEATURE:
<223> OTHER INFORMATION: scFv0032(nucleotide)

<400> SEQUENCE: 44
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaaa gggccactgg catcccagcc    180
aggttcagtg gcagtgggtc tgggacagac ttcactctca ccatcagcag cctagagcct    240
gaagattttg cagtttatta ctgtcagcag gccagtgccc tccctctcac ttttggcgga    300
gggaccaagg ttgagatcaa aggcagcacc agcggctccg gcaagcctgg ctctggcgag    360
ggcagcacaa agggagaagt gcagctggtg gagtctgggg gaggcttggt acagcctggc    420
aggtccctga gactcctgtg cagcctct ggattcacct ttgatgatta tgccatgcac    480
tgggtccggc aagctccagg aagggcctg gagtgggtct caggtattag ttggagtagt    540
ggtagcatag gctatgcgga ctctgtgaag ggccgattca ccatctccag agacaacgcc    600
aagaactccc tgtatctgca aatgaacagt ctgagagctg aggacacggc ggtgtactac    660
tgcgccaagg actcccctag aagggacagc ttcggaagca tagcattcga catatggggt    720
cagggtacaa tggtcaccgt cagctca                                        747

<210> SEQ ID NO 45
```

```
<211> LENGTH: 482
<212> TYPE: PRT
<213> ORGANISM: Artificial Sequence
<220> FEATURE:
<223> OTHER INFORMATION: CAR0009

<400> SEQUENCE: 45

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
130                 135                 140

Glu Thr Val Lys Ile Ser Cys Lys Ala Ser Gly Tyr Thr Phe Thr Asp
145                 150                 155                 160

Tyr Ser Ile Asn Trp Val Lys Arg Ala Pro Gly Lys Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Glu Thr Ser Ala Ser Thr Ala
        195                 200                 205

Tyr Leu Gln Ile Asn Asn Leu Lys Tyr Glu Asp Thr Ala Thr Tyr Phe
    210                 215                 220

Cys Ala Leu Asp Tyr Ser Tyr Ala Met Asp Tyr Trp Gly Gln Gly Thr
225                 230                 235                 240

Ser Val Thr Val Ser Ser Phe Val Pro Val Phe Leu Pro Ala Lys Pro
                245                 250                 255

Thr Thr Thr Pro Ala Pro Arg Pro Pro Thr Pro Ala Pro Thr Ile Ala
            260                 265                 270

Ser Gln Pro Leu Ser Leu Arg Pro Glu Ala Cys Arg Pro Ala Ala Gly
        275                 280                 285

Gly Ala Val His Thr Arg Gly Leu Asp Phe Ala Cys Asp Ile Tyr Ile
    290                 295                 300

Trp Ala Pro Leu Ala Gly Thr Cys Gly Val Leu Leu Leu Ser Leu Val
305                 310                 315                 320

Ile Thr Leu Tyr Cys Asn His Arg Asn Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380
```

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 46
<211> LENGTH: 1446
<212> TYPE: DNA
<213> ORGANISM: Artificial Sequence
<220> FEATURE:
<223> OTHER INFORMATION: CAR0009(nucleotide)

<400> SEQUENCE: 46

```
gacatcgtgc tgacccagag ccccccccagc ctggccatgt ctctgggcaa gagagccacc      60
atcagctgcc gggccagcga gagcgtgacc atcctgggca gccacctgat ccactggtat     120
cagcagaagc ccggccagcc ccccacccctg ctgatccagc tcgccagcaa tgtgcagacc     180
ggcgtgcccg ccagattcag cggcagcggc agcagaaccg acttcaccct gaccatcgac     240
cccgtggaag aggacgacgt ggccgtgtac tactgcctgc agagccggac catcccccgg     300
acctttggcg gaggcaccaa actggaaatc aagggcagca ccagcggctc cggcaagcct     360
ggctctggcg agggcagcac aaagggacag attcagctgg tgcagagcgg ccctgagctg     420
aagaaacccg gcgagacagt gaagatcagc tgcaaggcct ccggctacac cttcaccgac     480
tacagcatca ctgggtgaa agagcccct ggcaagggcc tgaagtggat gggctggatc     540
aacaccgaga aagagagcc cgcctacgcc tacgacttcc ggggcagatt cgccttcagc     600
ctggaaacca cgccagcac cgcctacctg cagatcaaca acctgaagta cgaggacacc     660
gccacctact ttgcgccct ggactacagc tacgccatgg actactgggg ccagggcacc     720
agcgtgaccg tgtccagctt cgtgcccgtg ttcctgcccg ccaaacctac caccaccccct     780
gcccctagac ctcccacccc agccccaaca atcgccagcc agcctctgtc tctgcggccc     840
gaagcctgta acctgctgc cggcggagcc gtgcacacca gaggcctgga cttcgcctgc     900
gacatctaca tctgggcccc tctggccggc acctgtggcg tgctgctgct gagcctggtg     960
atcacccctgt actgcaacca ccggaacaga agcaagcgga ccggctgct gcacagcgac    1020
tacatgaaca tgacccccaag acggcctggc cccaccccgga agcactacca gccttacgcc    1080
cctcccagag acttcgccgc ctaccggtcc agagtgaagt tcagcagatc cgccgacgcc    1140
cctgcctacc agcagggaca gaaccagctg tacaacgagc tgaacctggg cagacgggaa    1200
gagtacgacg tgctggacaa gcggagaggc cgggacccccg agatggggcgg aaagcccaga    1260
cggaagaacc cccaggaagg cctgtataac gaactgcaga agacaagat ggccgaggcc    1320
tacagcgaga tcggcatgaa gggcgagcgg aggcgcggca agggccacga tggcctgtac    1380
cagggcctga gcaccgccac caaggacacc tacgacgccc tgcacatgca ggccctgccc    1440
``` cccaga 1446

<210> SEQ ID NO 47
<211> LENGTH: 491
<212> TYPE: PRT
<213> ORGANISM: Artificial Sequence
<220> FEATURE:
<223> OTHER INFORMATION: CAR0041

<400> SEQUENCE: 47

Tyr Pro Tyr Asp Val Pro Asp Tyr Ala Asp Ile Val Leu Thr Gln Ser
1               5                   10                  15

Pro Pro Ser Leu Ala Met Ser Leu Gly Lys Arg Ala Thr Ile Ser Cys
            20                  25                  30

Arg Ala Ser Glu Ser Val Thr Ile Leu Gly Ser His Leu Ile His Trp
        35                  40                  45

Tyr Gln Gln Lys Pro Gly Gln Pro Pro Thr Leu Leu Ile Gln Leu Ala
    50                  55                  60

Ser Asn Val Gln Thr Gly Val Pro Ala Arg Phe Ser Gly Ser Gly Ser
65                  70                  75                  80

Arg Thr Asp Phe Thr Leu Thr Ile Asp Pro Val Glu Glu Asp Asp Val
                85                  90                  95

Ala Val Tyr Tyr Cys Leu Gln Ser Arg Thr Ile Pro Arg Thr Phe Gly
            100                 105                 110

Gly Gly Thr Lys Leu Glu Ile Lys Gly Ser Thr Ser Gly Ser Gly Lys
        115                 120                 125

Pro Gly Ser Gly Glu Gly Ser Thr Lys Gly Gln Ile Gln Leu Val Gln
    130                 135                 140

Ser Gly Pro Glu Leu Lys Lys Pro Gly Glu Thr Val Lys Ile Ser Cys
145                 150                 155                 160

Lys Ala Ser Gly Tyr Thr Phe Thr Asp Tyr Ser Ile Asn Trp Val Lys
                165                 170                 175

Arg Ala Pro Gly Lys Gly Leu Lys Trp Met Gly Trp Ile Asn Thr Glu
            180                 185                 190

Thr Arg Glu Pro Ala Tyr Ala Tyr Asp Phe Arg Gly Arg Phe Ala Phe
        195                 200                 205

Ser Leu Glu Thr Ser Ala Ser Thr Ala Tyr Leu Gln Ile Asn Asn Leu
    210                 215                 220

Lys Tyr Glu Asp Thr Ala Thr Tyr Phe Cys Ala Leu Asp Tyr Ser Tyr
225                 230                 235                 240

Ala Met Asp Tyr Trp Gly Gln Gly Thr Ser Val Thr Val Ser Ser Phe
                245                 250                 255

Val Pro Val Phe Leu Pro Ala Lys Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Asn His
                325                 330                 335

Arg Asn Arg Ser Lys Arg Ser Arg Leu Leu His Ser Asp Tyr Met Asn
            340                 345                 350

Met Thr Pro Arg Arg Pro Gly Pro Thr Arg Lys His Tyr Gln Pro Tyr

```
                355                 360                 365
Ala Pro Pro Arg Asp Phe Ala Ala Tyr Arg Ser Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 48
<211> LENGTH: 1473
<212> TYPE: DNA
<213> ORGANISM: Artificial Sequence
<220> FEATURE:
<223> OTHER INFORMATION: CAR0041(nucleotide)

<400> SEQUENCE: 48

```
tacccatacg atgttccaga ttacgctgac atcgtgctga cccagagccc ccccagcctg      60
gccatgtctc tgggcaagag agccaccatc agctgccggg ccagcgagag cgtgaccatc     120
ctgggcagcc acctgatcca ctggtatcag cagaagcccg ccagccccca ccctgctg      180
atccagctcg ccagcaatgt gcagaccggc gtgcccgcca gattcagcgg cagcggcagc     240
agaaccgact tcaccctgac catcgacccc gtggaagagg acgacgtggc cgtgtactac     300
tgcctgcaga gccggaccat ccccccggac ctttggcgga gcaccaaact ggaaatcaag     360
ggcagcacca cgggctccgg caagcctggc tctggcgagg gcagcacaaa gggacagatt     420
cagctggtgc agagcggccc tgagctgaag aaacccggcg agacagtgaa gatcagctgc     480
aaggcctccg gctacacctt caccgactac agcatcaact gggtgaaaag agcccctggc     540
aagggcctga gtggatgggc tggatcaac accgagacaa gagagcccgc ctacgcctac     600
gacttccggg gcagattcgc cttcagcctg gaaaccagcg ccagcaccgc ctacctgcag     660
atcaacaacc tgaagtacga ggacaccgcc acctactttt gcgccctgga ctacagctac     720
gccatggact actgggggcca gggcaccagc gtgaccgtgt ccagcttcgt gcccgtgttc     780
ctgcccgcca aacctaccac cacccctgcc cctagacctc ccacccccagc cccaacaatc     840
gccagccagc ctctgtctct gcggcccgaa gcctgtagac tgctgccgg cggagccgtg     900
cacaccagag gcctggactt cgcctgcgac atctacatct ggcccctct ggccggcacc     960
tgtgccgtgc tgctgctgag cctggtgatc accctgtact gcaaccaccg gaacagaagc    1020
aagcggagcc ggctgctgca cagcgactac atgaacatga ccccaagacg gcctggcccc    1080
acccggaagc actaccagcc ttacgcccct cccagagact cgccgccta ccggtccaga    1140
gtgaagttca gcagatccgc cgacgccct gcctaccagc agggacagaa ccagctgtac    1200
aacgagctga acctgggcag acgggaagag tacgacgtgc tggacaagcg agaggccgg    1260
gaccccgaga tgggcggaaa gcccagacgg aagaaccccc aggaaggcct gtataacgaa    1320
```

```
ctgcagaaag acaagatggc cgaggcctac agcgagatcg gcatgaaggg cgagcggagg    1380
cgcggcaagg gccacgatgg cctgtaccag ggcctgagca ccgccaccaa ggacacctac    1440
gacgccctgc acatgcaggc cctgcccccc aga                                 1473
```

<210> SEQ ID NO 49
<211> LENGTH: 494
<212> TYPE: PRT
<213> ORGANISM: Artificial Sequence
<220> FEATURE:
<223> OTHER INFORMATION: CAR0043

<400> SEQUENCE: 49

```
Tyr Pro Tyr Asp Val Pro Asp Tyr Ala Glu Ile Val Leu Thr Gln Ser
1               5                   10                  15

Pro Ala Thr Leu Ser Leu Ser Pro Gly Glu Arg Ala Thr Leu Ser Cys
            20                  25                  30

Arg Ala Ser Gln Ser Val Ser Ser Tyr Leu Ala Trp Tyr Gln Gln Lys
        35                  40                  45

Pro Gly Gln Ala Pro Arg Leu Leu Ile Tyr Asp Ala Ser Lys Arg Ala
    50                  55                  60

Thr Gly Ile Pro Ala Arg Phe Ser Gly Ser Gly Ser Gly Thr Asp Phe
65                  70                  75                  80

Thr Leu Thr Ile Ser Ser Leu Glu Pro Glu Asp Phe Ala Val Tyr Tyr
                85                  90                  95

Cys Gln Gln Ala Ser Ala Leu Pro Leu Thr Phe Gly Gly Gly Thr Lys
            100                 105                 110

Val Glu Ile Lys Gly Ser Thr Ser Gly Ser Gly Lys Pro Gly Ser Gly
        115                 120                 125

Glu Gly Ser Thr Lys Gly Glu Val Gln Leu Val Glu Ser Gly Gly Gly
    130                 135                 140

Leu Val Gln Pro Gly Arg Ser Leu Arg Leu Ser Cys Ala Ala Ser Gly
145                 150                 155                 160

Phe Thr Phe Asp Asp Tyr Ala Met His Trp Val Arg Gln Ala Pro Gly
                165                 170                 175

Lys Gly Leu Glu Trp Val Ser Gly Ile Ser Trp Ser Gly Ser Ile
            180                 185                 190

Gly Tyr Ala Asp Ser Val Lys Gly Arg Phe Thr Ile Ser Arg Asp Asn
        195                 200                 205

Ala Lys Asn Ser Leu Tyr Leu Gln Met Asn Ser Leu Arg Ala Glu Asp
    210                 215                 220

Thr Ala Val Tyr Tyr Cys Ala Lys Asp Ser Pro Arg Arg Asp Ser Phe
225                 230                 235                 240

Gly Ser Ile Ala Phe Asp Ile Trp Gly Gln Gly Thr Met Val Thr Val
                245                 250                 255

Ser Ser Phe Val Pro Val Phe Leu Pro Ala Lys Pro Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335
```

```
Cys Asn His Arg Asn Arg Ser Lys Arg Ser Arg Leu Leu His Ser Asp
                340                 345                 350

Tyr Met Asn Met Thr Pro Arg Pro Gly Pro Thr Arg Lys His Tyr
            355                 360                 365

Gln Pro Tyr Ala Pro Pro Arg Asp Phe Ala Ala Tyr Arg Ser Arg Val
370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 50
<211> LENGTH: 1482
<212> TYPE: DNA
<213> ORGANISM: Artificial Sequence
<220> FEATURE:
<223> OTHER INFORMATION: CAR0043(nucleotide)

<400> SEQUENCE: 50
tacccatacg atgttccaga ttacgctgaa attgtgttga cacagtctcc agccaccctg      60
tctttgtctc caggggaaag agccaccctc tcctgcaggg ccagtcagag tgttagcagc     120
tacttagcct ggtaccaaca gaaacctggc caggctccca ggctcctcat ctatgatgca     180
tccaaaaggg ccactggcat cccagccagg ttcagtggca gtgggtctgg gacagacttc     240
actctcacca tcagcagcct agagcctgaa gattttgcag tttattactg tcagcaggcc     300
agtgccctcc ctctcacttt tggcggaggg accaaggttg agatcaaagg cagcaccagc     360
ggctccggca gcctggctc tggcgagggc agcacaaagg agaagtgca gctggtggag      420 tctgggggag gcttggtaca gcctggcagg tccctgagac tctcctgtgc agcctctgga     480
ttcacctttg atgattatgc catgcactgg gtccggcaag ctccagggaa gggcctggag     540
tgggtctcag gtattagttg gagtagtggt agcataggct atgcggactc tgtgaagggc     600
cgattcacca tctccagaga caacgccaag aactccctgt atctgcaaat gaacagtctg     660
agagctgagg acacggcggt gtactactgc gccaaggact ccctagaag gacagcttc      720 ggaagcatag cattcgacat atggggtcag ggtacaatgg tcaccgtcag ctcattcgtg     780
cccgtgttcc tgcccgccaa acctaccacc ccctgccc ctagacctcc caccccagcc     840
ccaacaatcg ccagccagcc tctgtctctg cggcccgaag cctgtagacc tgctgccggc     900
ggagccgtgc acaccagagg cctggacttc gcctgcgaca tctacatctg gcccctctg     960 gccggcacct gtggcgtgct gctgctgagc ctggtgatca ccctgtactg caaccaccgg    1020
aacagaagca gcggagccg gctgctgcac agcgactaca tgaacatgac ccaagacgg    1080 cctggcccca cccggaagca ctaccagcct tacgcccctc cagagactt cgccgcctac    1140
```

```
cggtccagag tgaagttcag cagatccgcc gacgccctg cctaccagca gggacagaac    1200
cagctgtaca cgagctgaa cctgggcaga cgggaagagt acgacgtgct ggacaagcgg    1260
agaggccggg accccgagat gggcggaaag cccagacgga agaaccccca ggaaggcctg    1320
tataacgaac tgcagaaaga caagatggcc gaggcctaca gcgagatcgg catgaagggc    1380
gagcggaggc gcggcaaggg ccacgatggc ctgtaccagg gcctgagcac cgccaccaag    1440
gacacctacg acgccctgca catgcaggcc ctgccccca ga                       1482
```

<210> SEQ ID NO 51
<211> LENGTH: 486
<212> TYPE: PRT
<213> ORGANISM: Artificial Sequence
<220> FEATURE:
<223> OTHER INFORMATION: CAR0097

<400> SEQUENCE: 51

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ala Ser Ala Leu Pro Leu
                85                  90                  95

Thr Phe Gly Gly Gly Thr Lys Val Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Leu Val Glu Ser Gly Gly Gly Leu Val Gln Pro Gly Arg Ser Leu Arg
130                 135                 140

Leu Ser Cys Ala Ala Ser Gly Phe Thr Phe Asp Asp Tyr Ala Met His
145                 150                 155                 160

Trp Val Arg Gln Ala Pro Gly Lys Gly Leu Glu Trp Val Ser Gly Ile
                165                 170                 175

Ser Trp Ser Ser Gly Ser Ile Gly Tyr Ala Asp Ser Val Lys Gly Arg
            180                 185                 190

Phe Thr Ile Ser Arg Asp Asn Ala Lys Asn Ser Leu Tyr Leu Gln Met
        195                 200                 205

Asn Ser Leu Arg Ala Glu Asp Thr Ala Val Tyr Tyr Cys Ala Lys Asp
    210                 215                 220

Ser Pro Arg Arg Asp Ser Phe Gly Ser Ile Ala Phe Asp Ile Trp Gly
225                 230                 235                 240

Gln Gly Thr Met Val Thr Val Ser Ser Phe Val Pro Val Phe Leu Pro
                245                 250                 255

Ala Lys Pro Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300
```

| | | | | | | | | | | | |
|---|---|---|---|---|---|---|---|---|---|---|---|
| Ile | Tyr | Ile | Trp | Ala | Pro | Leu | Ala | Gly | Thr | Cys | Gly | Val | Leu | Leu | Leu |
| 305 | | | | 310 | | | | 315 | | | | 320 |

Ser Leu Val Ile Thr Leu Tyr Cys Asn His Arg Asn Lys Arg Gly Arg
              325                 330                 335

Lys Lys Leu Leu Tyr Ile Phe Lys Gln Pro Phe Met Arg Pro Val Gln
              340                 345                 350

Thr Thr Gln Glu Glu Asp Gly Cys Ser Cys Arg Phe Pro Glu Glu Glu
              355                 360                 365

Glu Gly Gly Cys Glu Leu Arg Val Lys Phe Ser Arg Ser Ala Asp Ala
              370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
              405                 410                 415

Pro Glu Met Gly Gly Lys Pro Arg Arg Lys Asn Pro Gln Glu Gly Leu
              420                 425                 430

Tyr Asn Glu Leu Gln Lys Asp Lys Met Ala Glu Ala Tyr Ser Glu Ile
              435                 440                 445

Gly Met Lys Gly Glu Arg Arg Arg Gly Lys Gly His Asp Gly Leu Tyr
450                 455                 460

Gln Gly Leu Ser Thr Ala Thr Lys Asp Thr Tyr Asp Ala Leu His Met
465                 470                 475                 480

Gln Ala Leu Pro Pro Arg
              485

```
<210> SEQ ID NO 52
<211> LENGTH: 1458
<212> TYPE: DNA
<213> ORGANISM: Artificial Sequence
<220> FEATURE:
<223> OTHER INFORMATION: CAR0097(nucleotide)

<400> SEQUENCE: 52
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaaa gggccactgg catcccagcc     180
aggttcagtg gcagtgggtc tgggacagac ttcactctca ccatcagcag cctagagcct     240
gaagattttg cagtttatta ctgtcagcag gccagtgccc tcctctcac ttttggcgga     300
gggaccaagg ttgagatcaa aggcagcacc agcggctccg gcaagcctgg ctctggcgag     360
ggcagcacaa agggagaagt gcagctggtg gagtctgggg gaggcttggt acagcctggc     420
aggtccctga gactctcctg tgcagcctct ggattcacct tgatgattta tgccatgcac     480
tgggtccggc aagctccagg aagggcctg gagtgggtct caggtattag ttggagtagt     540
ggtagcatag gctatgcgga ctctgtgaag ggccgattca ccatctccag agacaacgcc     600
aagaactccc tgtatctgca aatgaacagt ctgagagctg aggacacggc ggtgtactac     660
tgcgccaagg actcccctag aagggacagc ttcggaagca tagcattcga catatggggt     720
cagggtacaa tggtcaccgt cagctcattc gtgcccgtgt tcctgcccgc caaacctacc     780
accacccctg cccctagacc tcccacccca gccccaacaa tcgccagcca gcctctgtct     840
ctgcggcccg aagcctgtag acctgctgcc ggcggagccg tgcacaccag aggcctggac     900
ttcgcctgcg acatctacat ctgggcccct ctggccggca cctgtggcgt gctgctgctg     960
agcctggtga tcaccctgta ctgcaaccac cggaacaaac ggggcagaaa gaaactcctg    1020
```

-continued

```
tatatattca aacaaccatt tatgagacca gtacaaacta ctcaagagga agatggctgt    1080
agctgccgat ttccagaaga agaagaagga ggatgtgaac tgagagtgaa gttcagcaga    1140
tccgccgacg cccctgccta ccagcaggga cagaaccagc tgtacaacga gctgaacctg    1200
ggcagacggg aagagtacga cgtgctggac aagcggagag gccgggaccc cgagatgggc    1260
ggaaagccca gacggaagaa cccccaggaa ggcctgtata acgaactgca gaaagacaag    1320
atggccgagg cctacagcga gatcggcatg aagggcgagc ggaggcgcgg caagggccac    1380
gatggcctgt accagggcct gagcaccgcc accaaggaca cctacgacgc cctgcacatg    1440
caggccctgc cccccaga                                                  1458
```